(12) United States Patent
Menozzi et al.

(10) Patent No.: US 9,464,070 B2
(45) Date of Patent: Oct. 11, 2016

(54) STERICALLY HINDERED AMINE STABILIZER

(71) Applicant: BASF SE, Ludwigshafen (DE)

(72) Inventors: Edoardo Menozzi, Basel (CH); Massimiliano Sala, Castelnuovo Rangone (IT); Anna Bassi, Ludwigshafen (DE); Holger Hoppe, Lorrach (DE); Björn Ludolph, Ludwigshafen (DE); Gérard Lips, Huningue (FR)

(73) Assignee: BASF SE, Ludwigshafen (DE)

( * ) Notice: Subject to any disclaimer, the term of this patent is extended or adjusted under 35 U.S.C. 154(b) by 50 days.

(21) Appl. No.: 14/444,495

(22) Filed: Jul. 28, 2014

(65) Prior Publication Data
US 2014/0336313 A1  Nov. 13, 2014

Related U.S. Application Data

(63) Continuation of application No. 13/394,431, filed as application No. PCT/EP2010/062664 on Aug. 31, 2010, now Pat. No. 8,895,647.

(30) Foreign Application Priority Data

Sep. 10, 2009  (EP) ..................... 09169926

(51) Int. Cl.
C08K 5/3492 (2006.01)
C07D 401/14 (2006.01)

(52) U.S. Cl.
CPC ......... C07D 401/14 (2013.01); C08K 5/34926 (2013.01)

(58) Field of Classification Search
None
See application file for complete search history.

(56) References Cited

U.S. PATENT DOCUMENTS

| 5,096,950 | A | 3/1992 | Galbo et al. |
| 5,844,026 | A | 12/1998 | Galbo et al. |
| 6,117,995 | A | 9/2000 | Zedda et al. |
| 7,947,832 | B2 | 5/2011 | Wood et al. |
| 8,076,478 | B2 | 12/2011 | Mita et al. |
| 2009/0199351 | A1 | 8/2009 | Wood et al. |
| 2012/0108711 | A1 | 5/2012 | Sala et al. |

FOREIGN PATENT DOCUMENTS

EP  1 840 127  10/2007

*Primary Examiner* — Ling Choi
*Assistant Examiner* — Catherine S Branch
(74) *Attorney, Agent, or Firm* — Oblon, McClelland, Maier & Neustadt, L.L.P.

(57) ABSTRACT

The present invention relates to oxygen-substituted sterically hindered amines of the formulae I or II: (II), wherein, for example, $F_2$, $R_3$, $R_5$, $R_6$, $R_8$, $R_9$, $R_{11}$, $R_{12}$, $R_{13}$, $R_{14}$ are n-butyl: $Z_1$ to $Z_{10}$ are propoxy and $R_1$, $R_4$, $R_7$, $R_{10}$, $R_{13}$ are 2,2,6,6-tetramethyl-1-propoxy-piperidin-4-yl. Compositions comprising compounds of formulae I or II and an organic material, which is susceptible to oxidative, thermal or light-induced degradation, are further disclosed. Optionally, further additives are contained.

15 Claims, No Drawings

STERICALLY HINDERED AMINE STABILIZER

This application is a continutation application of U.S. Ser. No. 13/394,431 filed on May 14, 2012.

Sterically hindered amines are known to be efficient stabilizers for organic materials against the harmful effect of light and heat—especially for synthetic polymers like polyolefins. For example, agricultural films produced from polyolefins are stabilized by sterically hindered amine stabilizers, since light transmission has got a major Impact on the growth of crops and a sustainable light transmission depends on the long-term stability of the film.

The sterically hindered nitrogen atom of the sterically hindered amine can either possess a hydrogen atom, i.e. a secondary amine, or can be substituted further for example by an oxygen atom like in the case of an alkylether. The basicity of the sterically hinderd amine is reduced in case of substitution of its nitrogen atom with an oxygen atom. These oxygen-substituted sterically hindered amines proved to be especially useful in applications where exposure to acids takes place. The acids or traces of acid might be present from the start—e.g. an acid-cured coating resin—or be released over time. The latter one can be an acid release from another component of the organic material, for example specific halogen-containing flame retardants, or the immission of traces of acid from the external environment, for example by exposure to vapours of specific crop protection agents like vapam.

Many different sterically hindered amine stabilizers—with or without oxygen-substitution—have been disclosed in prior art.

In U.S. Pat. No. 5,096,950, oxygen-substituted sterically hindered amine stabilizers useful as stabilizers for polyolefin compositions are disclosed.

In U.S. Pat. No. 5,844,026, oxygen-substituted sterically hindered amine stabilizers useful as stabilizers for polyolefin compositions are disclosed.

In U.S. Pat. No. 6,117,995, oxygen-substituted sterically hindered amine stabilizers useful as stabilizers for organic material are disclosed.

In EP-A-1840127, sterically hindered amine stabilizers useful as stabilizers for organic material are disclosed.

However, there is still a need for further oxygen-substituted sterically hindered amine stabilizers, which provide a further improvement of the long-term stabilization of organic materials.

Another aspect is the replacement of polymeric oxygen-substituted sterically hindered amine stabilizers, which are by definition multi-component mixtures, by more well-defined, in principle single molecule type of oxygen-substituted sterically hindered amine stabilizers. This is desirable in regard to a more precise and better manageable synthesis and also a more straightforward analytical characterization afterwards. Furthermore, better fine-tuning of physical-chemical properties is possible for a more single-molecule type of material.

It has now been found that a specific class of oxygen-substituted sterically hindered amine stabilizer is fulfilling the above stated requirements.

An embodiment of this invention is a compound of formula I

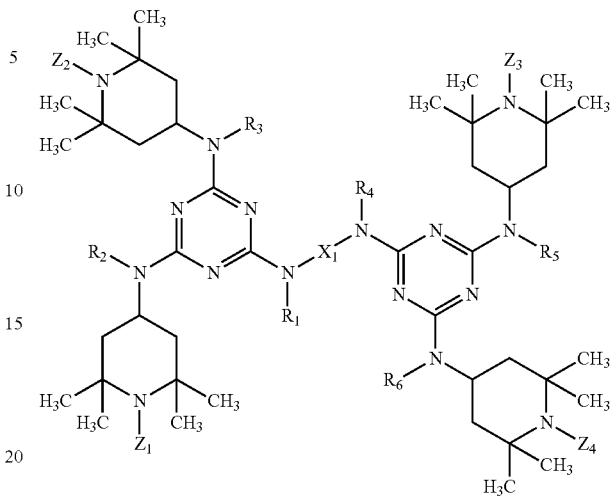

of formula II

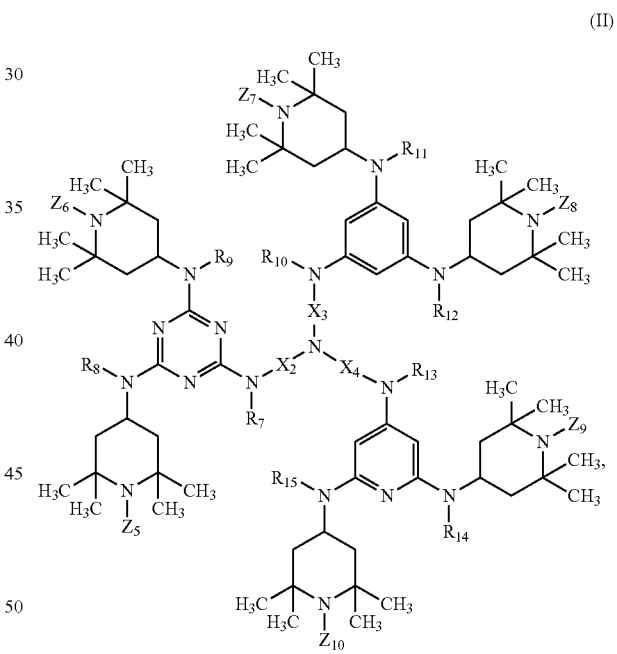

wherein $R_1$ is a group of formula III

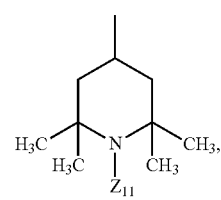

hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$R_4$ is a group of formula IV

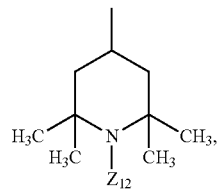

(IV)

hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$R_2$, $R_3$, $R_5$ and $R_6$ are each independently from each other $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$Z_1$, $Z_2$, $Z_3$, $Z_4$, $Z_{11}$ and $Z_{12}$ are each independently from each other $C_1$-$C_{18}$ alkyloxy, $C_3$-$C_{18}$ alkenyloxy, $C_3$-$C_{18}$ alkynyloxy, $C_6$-$C_{10}$ aryloxy, $C_7$-$C_9$ aralkyloxy or $C_7$-$C_{20}$ aralkyloxy substituted by $C_1$-$C_4$ alkyl or $C_6$-$C_{10}$ aryl;

$X_1$ is $C_2$-$C_{12}$ alkylene or $C_3$-$C_{12}$ alkylene substituted by hydroxyl; or $R_7$ is a group of formula V

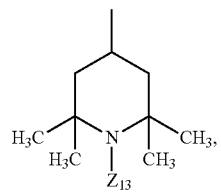

(V)

hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$R_{10}$ is a group of formula VI

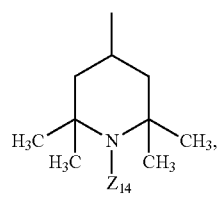

(VI)

hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$R_{13}$ is a group of formula VII

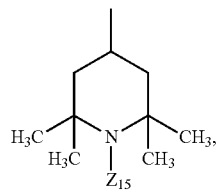

(VII)

hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$R_8$, $R_9$, $R_{11}$, $R_{12}$, $R_{14}$ and $R_{15}$ are each independently from each other $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$Z_5$, $Z_6$, $Z_7$, $Z_8$, $Z_9$, $Z_{10}$, $Z_{11}$, $Z_{13}$, $Z_{14}$ and $Z_{15}$ are each independently from each other $C_1$-$C_{18}$ alkyloxy, $C_3$-$C_{18}$ alkenyloxy, $C_3$-$C_{12}$ cycloalkyloxy, $C_5$-$C_8$ cycloalkenyloxy, $C_6$-$C_{10}$ bicycloalkyloxy, $C_3$-$C_{18}$ alkynyloxy, $C_6$-$C_{10}$ aryloxy, $C_7$-$C_9$ aralkyloxy or $C_7$-$C_{20}$ aralkyloxy substituted by $C_1$-$C_4$ alkyl or $C_6$-$C_{10}$ aryl;

$X_2$, $X_3$ and $X_4$ are each independently from each other $C_2$-$C_{12}$ alkylene or $C_3$-$C_{12}$ alkylene substituted by hydroxyl.

$C_1$-$C_8$ alkyl comprises linear and branched alkyl. Examples are methyl, ethyl, n-propyl, 1-methylethyl, n-butyl, 2-methylpropyl, 1-methylpropyl, tert-butyl, pentyl, 1-methylbutyl, 2-methylbutyl, 3-methylbutyl, 1,1-dimethylpropyl, 1-ethylpropyl, tert-butylmethyl, hexyl, 1-methylpentyl, heptyl, isoheptyl, 2-ethylpentyl, 1-propylbutyl, octyl, isooctyl, 1-ethylhexyl, 2-ethylhexyl, 1,1,3,3-tetramethylbutyl, 2,4,4-trimethylpentyl, nonyl, isononyl, neononyl, undecyl, lauryl, tridecyl, tetradecyl, pentadecyl, hexadecyl and octadecyl.

Preferred is $C_1$-$C_{12}$ alkyl, especially $C_1$-$C_8$ alkyl, in particular $C_1$-$C_4$ alkyl. A preferred example is butyl, especially n-butyl.

$C_3$-$C_{18}$ alkenyl comprises linear and branched alkenyl including possible E- and Z-isomers. Examples are allyl, 3-methyl-but-2-enyl, dec-9-enyl, hexadec-9-enyl, octadec-9-enyl. Preferred is $C_3$-$C_{12}$ alkenyl. A preferred example is allyl.

$C_3$-$C_{12}$ cycloalkyl comprises unsubstituted and substituted, i.e. by one or more $C_1$-$C_4$ alkyl, cycloalkyl. Examples are cyclopropyl, 3-methylcyclopropyl, 2,2,3,3-tetramethylcyclopropyl, cyclobutyl, cyclopentyl, cyclohexyl, 1-methylcyclohexyl, 2-methylcyclohexyl, 3-methylcyclohexyl, 4-methylcyclohexyl, 4-tert-butylcyclohexyl and cycloheptyl.

Preferred are $C_3$-$C_6$ cycloalkyl, particularly $C_5$-$C_6$ cycloalkyl. A preferred example is cyclohexyl.

$C_5$-$C_8$ cycloalkenyl comprises unsubstituted and substituted, i.e. by one or more $C_1$-$C_4$ alkyl, cycloalkenyl. Examples are cyclopentenyl, cyclohexenyl, cycloheptenyl and cyclooctenyl.

$C_6$-$C_{10}$ bicycloalkyl comprises unsubstituted and substituted, i.e. by one or more $C_1$-$C_4$ alkyl, bicycloalkyl. Examples are bicyclo[2.2.1]heptyl, bicyclo[3.1.1]heptyl, 3-methyl-bicyclo[3.1.1]-heptyl and 1,7,7-trimethylbicyclo[2.2.1]heptyl.

$C_3$-$C_{18}$ alkynyl are exemplified by propargyl, but-3-inyl, hex-5-inyl, oct-7-inyl, dec-9-inyl, dodec-11-inyl, tetradec-13-inyl, hexadec-15-inyl and octadec-17-inyl.

Preferred is $C_3$-$C_{12}$ alkinyl. A preferred example is propargyl.

$C_6$-$C_{10}$ aryl comprises unsubstituted and substituted, i.e. by one or more $C_1$-$C_4$ alkyl, aryl. Examples are phenyl, 3-methylphenyl, 4-methylphenyl, dimethylphenyl, 3-ethylphenyl, 4-ethylphenyl, iso-propylphenyl, tert-butylphenyl, naphtyl and biphenyl.

Preferred is unsubstituted or substituted phenyl, in particular unsubstituted and para-substituted phenyl.

$C_7$-$C_9$ aralkyl is exemplified by benzyl, phenylethyl and phenylpropyl. A preferred example is benzyl.

$C_7$-$C_{20}$ aralkyl substituted by $C_1$-$C_4$ alkyl or $C_6$-$C_{10}$ aryl is exemplified by α-methylbenzyl, 3-methylbenzyl, 4-methylbenzyl, α,α-dimethylbenzyl, α-ethylbenzyl, 4-ethylbenzyl, 4-propylbenzyl, 4-iso-propyl-benzyl, 4-tert-butylbenzyl and diphenylmethyl.

$C_1$-$C_{18}$ alkyloxy comprises unsubstituted and substituted, i.e. by $C_1$-$C_9$ alkyl, alkyloxy. Examples are methyloxy, ethyloxy, propyloxy (=propoxy), butyloxy, hexyloxy, octyloxy and undecyloxy.

Preferred is $C_1$-$C_{12}$ alkyloxy. Preferred examples are methyloxy, ethyloxy, propyloxy, octyloxy and undecyloxy. Especially preferred is propyloxy.

Preferred is $C_1$-$C_{18}$ alkyloxy, wherein in case of $C_3$-$C_{18}$ alkyloxy both carbon atoms in α- and β-position next to the oxygen are not branched. Examples are methyloxy, ethyloxy, n-propyloxy, n-butyloxy, n-pentyloxy, 3-methylbutyloxy, n-hexyloxy, 3-methylpentyloxy, 4-methylpentyloxy, n-heptyloxy, 3-methylhexyloxy, 4-methylhexyloxy, 5-methylhexyloxy, 3-ethylpentyloxy, 3,4-dimethylpentyloxy, n-octyloxy, 3-methylheptyloxy, 4-methylheptyloxy, 5-methylheptyloxy, 6-methylheptyloxy, 3-ethylhexyloxy, 4-ethylhexyloxy, 3,4-dimethylhexyloxy, 3,5-dimethylhexyloxy, n-nonyloxy, 3-methyloctyloxy, 4-methyloctyloxy, 5-methyloctyloxy, 6-methyloctyloxy, 7-methyloctyloxy, 3-ethylheptyloxy, 4-ethylheptyloxy, 5-ethylheptyloxy, 3,4-dimethylheptyloxy, 3,5-dimethylheptyloxy, 3,6-dimethylheptyloxy, 4,5-dimethylheptyloxy, 4,6-dimethylheptyloxy, 5,6-dimethylheptyloxy, n-undecyloxy, n-lauryloxy, n-tridecyloxy, n-tetradecyloxy, n-pentadecyloxy, n-hexadecyloxy and n-octadecyloxy.

Preferred is $C_1$-$C_{12}$ alkyloxy, wherein in case of $C_3$-$C_{12}$ alkyloxy both carbon atoms in α- and β-position next to the oxygen are not branched.

Preferred is $C_1$-$C_8$ alkyloxy, wherein in case of $C_3$-$C_8$ alkyloxy both carbon atoms in α- and β-position next to the oxygen are not branched.

Preferred is linear $C_1$-$C_{12}$ alkyloxy. Examples are methyloxy, ethyloxy, n-propyloxy, n-butyloxy, n-pentyloxy, n-hexyloxy, n-heptyloxy, n-octyloxy, n-nonyloxy, n-undecyloxy and n-lauryloxy.

Especially preferred are methyloxy, ethyloxy and n-propyloxy.

$C_3$-$C_{18}$ alkenyloxy comprises unsubstituted and substituted, i.e. by $C_1$-$C_9$ alkyl, $C_3$-$C_{18}$ alkenyloxy. Examples are prop-2-enyloxy, prop-1-enyloxy, but-2-enyloxy and 3-methyl-but-2-enyl.

Preferred is $C_3$-$C_{12}$ alkenyloxy. A preferred example is prop-2-enyloxy.

$C_3$-$C_{12}$ cycloalkyloxy is exemplified by cyclopentyloxy, cyclohexyloxy, cycloheptyloxy and cyclooctyloxy.

Preferred is $C_5$-$C_8$ cycloalkyloxy. A preferred example is cyclohexyloxy.

$C_5$-$C_8$ cycloalkenyloxy is exemplified by cyclopentenyloxy, cyclohexenyloxy, cycloheptenyloxy and cylcooctenyloxy.

Preferred is $C_5$-$C_7$ cycloalkenyloxy. A preferred example is cyclohexenyloxy.

$C_6$-$C_{10}$ bicycloalkyloxy is exemplified by bicyclo[2.2.1]heptyloxy, bicyclo[3.1.1]heptyloxy, 3-methyl-bicyclo[3.1.1]heptyloxy and 1,7,7-trimethylbicyclo[2.2.1]heptyloxy.

$C_3$-$C_{18}$ alkynyloxy is exemplified by propargyloxy.

$C_6$-$C_{10}$ aryloxy is exemplified by phenyloxy, napthyloxy and biphenyloxy.

$C_7$-$C_9$ aralkyloxy is exemplified by benzyloxy, 2-phenylethyl and 3-phenylpropyl.

A preferred example is benzyloxy.

$C_7$-$C_{20}$ aralkyloxy substituted by $C_1$-$C_4$ alkyl or $C_6$-$C_{11}$ aryl is exemplified by α-methylbenzyloxy, 3-methylbenzyloxy, 4-methylbenzyloxy, α,α-dimethylbenzyloxy, α-ethylbenzyloxy, 4-ethylbenzyloxy, 4-propylbenzyloxy, 4-iso-propyl-benzyloxy, 4-tert-butylbenzyloxy and diphenylmethyloxy.

$C_2$-$C_{12}$ alkylene comprises unsubstituted and substituted, i.e. by one or more $C_1$-$C_4$ alkyl, alkylene. Examples are ethylene, propylene, 1-methylethylene, butylene, pentylene, 2-methylbutylene, hexamethylene and octamethylene.

Preferred are $C_2$-$C_8$ alkylene, in particular $C_2$-$C_6$ alkylene. Preferred examples are hexamethylene, propylene and ethylene.

$C_3$-$C_{12}$ alkylene substituted by hydroxyl comprises no further substituted and further substituted, i.e. by one or more $C_1$-$C_4$ alkyl, alkylene substituted by hydroxyl. Examples are 2-hydroxypropylene, 2-hydroxy-butylene, 2,3-dihydroxybutylene, 2,5-hexamethylene and 2-hydroxy-2-methylpropylene.

A preferred example is 2-hydroxypropylene.

Preferred is a compound of formula I.

Preferred is a compound of formula II.

Preferred is a compound of formula I or formula II, wherein $R_1$ is a group of formula III, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;

$R_4$ is a group of formula IV, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;

$R_2$, $R_3$, $R_5$ and $R_6$ are each independently from each other $C_1$-$C_{12}$ alkyl, $C_3$-$C_{12}$ alkenyl, $C_5$-$C_8$ cycloalkyl, $C_5$-$C_7$ cycloalkenyl or benzyl;

$Z_1$, $Z_2$, $Z_3$, $Z_4$, $Z_{14}$ and $Z_{12}$ are each independently from each other $C_1$-$C_{12}$ alkyloxy, $C_3$-$C_{12}$ alkenyloxy or benzyloxy;

$X_1$ is $C_2$-$C_8$ alkylene; or $R_7$ is a group of formula V, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;

$R_{10}$ is a group of formula VI, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;

$R_{13}$ is a group of formula VII, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;

$R_8$, $R_9$, $R_{11}$, $R_{12}$, $R_{14}$ and $R_{15}$ are each independently from each other $C_1$-$C_{12}$ alkyl, $C_3$-$C_{12}$ alkenyl, $C_5$-$C_8$ cycloalkyl, $C_5$-$C_7$ cycloalkenyl or benzyl;

$Z_5$, $Z_6$, $Z_7$, $Z_8$, $Z_9$, $Z_{10}$, $Z_{13}$, $Z_{14}$ and $Z_{15}$ are each independently from each other $C_1$-$C_{12}$ alkyloxy, $C_3$-$C_{12}$ alkenyloxy, $C_5$-$C_8$ cycloalkyloxy, $C_5$-$C_7$ cycloalkenyloxy, benzyloxy;

$X_2$, $X_3$ and $X_4$ are each independently from each other $C_2$-$C_6$ alkylene.

Especially preferred is a compound of formula I or formula II, wherein $R_2$, $R_3$, $R_5$ and $R_6$ are each independently from each other $C_1$-$C_{12}$ alkyl; or $R_8$, $R_9$, $R_{11}$, $R_{12}$, $R_{14}$ and $R_{15}$ are each independently from each other $C_1$-$C_{12}$ alkyl.

In particular, a compound of formula I or formula II is preferred, wherein
$R_1$ is a group of formula III and $R_4$ is a group of formula IV; or
$R_7$ is a group of formula V, $R_{10}$ is a group of formula VI and $R_{13}$ is a group of formula VII.

Furthermore preferred is a compound of formula I or formula II, wherein
$Z_1$, $Z_2$, $Z_3$, $Z_4$, $Z_{11}$ and $Z_{12}$ are each independently from each other methyloxy, ethyloxy, propyloxy, octyloxy, undecyloxy or prop-2-enyloxy; or
$Z_5$, $Z_6$, $Z_7$, $Z_8$, $Z_9$, $Z_{10}$, $Z_{13}$, $Z_{14}$ and $Z_{15}$ are independently from each other methyloxy, ethyloxy, propyloxy, octyloxy, undecyloxy, cyclohexyloxy or prop-2-enyloxy.

Preferred is also a compound of formula I or II, wherein
$R_1$ and $R_4$ are each independently from each other hydrogen, $C_1$-$C_{12}$ alkyl or $C_5$-$C_8$ cycloalkyl; or
$R_7$, $R_{10}$ and $R_{13}$ are each independently from each other hydrogen, $C_1$-$C_{12}$ alkyl or $C_5$-$C_8$ cycloalkyl.

Preference is given to a compound of formula I or formula II, wherein
$X_1$ is $C_2$-$C_6$ alkylene; or
$X_2$, $X_3$ and $X_4$ are $C_2$-$C_6$ alkylene.

In particular desirable is a compound of formula I or formula II, wherein
$X_1$ is hexamethylene; or
$X_2$, $X_3$ and $X_4$ are ethylene.

Preferred is also a compound of formula I or formula II, wherein
$R_2$, $R_3$, $R_5$ and $R_6$ are butyl; or
$R_8$, $R_9$, $R_{11}$, $R_{12}$, $R_{13}$ and $R_{15}$ are butyl.

Preferred is a compound of formula I or formula II, wherein
$R_1$ is a group of formula III or hydrogen;
$R_4$ is a group of formula IV or hydrogen;
$R_2$, $R_3$, $R_5$ and $R_6$ are each independently from each other $C_1$-$C_{12}$ alkyl;
$Z_1$, $Z_2$, $Z_3$, $Z_4$, $Z_{11}$ and $Z_{12}$ are each independently from each other $C_1$-$C_{12}$ alkyloxy;
$X_1$ is $C_2$-$C_8$ alkylene; or
$R_7$ is a group of formula V or hydrogen;
$R_{10}$ is a group of formula VI or hydrogen;
$R_{13}$ is a group of formula VII or hydrogen;
$R_8$, $R_9$, $R_{11}$, $R_{12}$, $R_{14}$ and $R_{15}$ are each independently from each other $C_1$-$C_{12}$ alkyl;
$Z_5$, $Z_6$, $Z_7$, $Z_8$, $Z_9$, $Z_{10}$, $Z_{13}$, $Z_{14}$ and $Z_{15}$ are each independently from each other $C_1$-$C_{12}$ alkyloxy;
$X_2$, $X_3$ and $X_4$ are each independently from each other $C_2$-$C_6$ alkylene.

Very preferred is also a compound of formula I or formula II, wherein
$R_1$ is a group of formula III and $R_4$ is a group of formula IV,
$R_2$, $R_3$, $R_5$ and $R_6$ are butyl,
$Z_1$, $Z_2$, $Z_3$, $Z_4$, $Z_{11}$ and $Z_{12}$ are methyloxy, ethyloxy, propyloxy, octyloxy or undecyloxy,
$X_1$ is hexamethylene; or
$R_7$ is a group of formula V, $R_{10}$ is a group of formula VI and $R_{13}$ is a group of formula VII,
$R_8$, $R_9$, $R_{11}$, $R_{12}$, $R_{13}$ and $R_{15}$ are butyl,
$Z_5$, $Z_6$, $Z_7$, $Z_8$, $Z_9$, $Z_{10}$, $Z_{13}$, $Z_{14}$ and $Z_{15}$ are methyloxy, ethyloxy, propyloxy, octyloxy, undecyloxy or cyclohexyloxy,
$X_2$, $X_3$ and $X_4$ are ethylene.

Preferred is a compound of formula I or formula II, wherein
$R_1$ is a group of formula III, hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;
$R_4$ is a group of formula IV, hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;
$R_2$, $R_3$, $R_5$ and $R_6$ are each independently from each other $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;
$Z_1$, $Z_2$, $Z_3$, $Z_4$, $Z_{11}$ and $Z_{12}$ are each independently from each other $C_1$-$C_{18}$ alkyloxy, wherein in case of $C_3$-$C_{18}$ alkyloxy both carbon atoms in α- and β-position next to the oxygen are not branched;
$X_1$ is $C_2$-$C_{12}$ alkylene or $C_3$-$C_{12}$ alkylene substituted by hydroxyl; or
$R_7$ is a group of formula V, hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_{20}$ aralkyl or $C_7$-$C_{20}$ aralkyl substituted by $C_1$-$C_4$ alkyl or $C_6$-$C_{10}$ aryl;
$R_{10}$ is a group of formula VI, hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;
$R_{13}$ is a group of formula VII, hydrogen, $C_1$-$C_{18}$ alkyl, $C_3$-$C_{18}$ alkenyl, $C_3$-$C_2$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;
$R_8$, $R_9$, $R_{11}$, $R_{12}$, $R_{14}$ and $R_{15}$ are each independently from each other $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;
$Z_5$, $Z_6$, $Z_7$, $Z_8$, $Z_9$, $Z_{10}$, $Z_{13}$, $Z_{14}$ and $Z_{15}$ are each independently from each other $C_1$-$C_{18}$ alkyloxy, wherein in case of $C_3$-$C_{18}$ alkyloxy both carbon atoms in α- and β-position next to the oxygen are not branched;
$X_2$, $X_3$ and $X_4$ are each independently from each other $C_2$-$C_{12}$ alkylene or $C_3$-$C_{12}$ alkylene substituted by hydroxyl.

Preferred is a compound of formula I or formula II, wherein
$R_1$ is a group of formula III, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;
$R_4$ is a group of formula IV, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;
$R_2$, $R_3$, $R_5$ and $R_6$ are each independently from each other $C_1$-$C_{12}$ alkyl, $C_3$-$C_{12}$ alkenyl, $C_5$-$C_7$ cycloalkyl, $C_5$-$C_7$ cycloalkenyl or benzyl;
$Z_1$, $Z_2$, $Z_3$, $Z_4$, $Z_{11}$ and $Z_{12}$ are each independently from each other $C_1$-$C_{12}$ alkyloxy, wherein in case of $C_3$-$C_{12}$ alkyloxy both carbon atoms in α- and β-position next to the oxygen are not branched;
$X_1$ is $C_2$-$C_8$ alkylene; or
$R_7$ is a group of formula V, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;
$R_{10}$ is a group of formula VI, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;

$R_{13}$ is a group of formula VII, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;

$R_8$, $R_9$, $R_{11}$, $R_{12}$, $R_{14}$ and $R_{15}$ are each independently from each other $C_1$-$C_{12}$ alkyl, $C_3$-$C_{12}$ alkenyl, $C_5$-$C_8$ cycloalkyl, $C_5$-$C_7$ cycloalkenyl or benzyl;

$Z_5$, $Z_6$, $Z_7$, $Z_8$, $Z_9$, $Z_{10}$, $Z_{13}$, $Z_{14}$ and $Z_{15}$ are each independently from each other $C_1$-$C_{12}$ alkyloxy, wherein in case of $C_3$-$C_{12}$ alkyloxy both carbon atoms in α- and β-position next to the oxygen are not branched;

$X_2$, $X_3$ and $X_4$ are each independently from each other $C_2$-$C_6$ alkylene.

Preferred is a compound of formula I or formula II, wherein
$R_1$ is a group of formula III or hydrogen;
$R_4$ is a group of formula IV or hydrogen;
$R_2$, $R_3$, $R_5$ and $R_6$ are each independently from each other $C_1$-$C_{12}$ alkyl;
$Z_1$, $Z_2$, $Z_3$, $Z_4$, $Z_{11}$ and $Z_{12}$ are each independently from each other $C_1$-$C_{12}$ alkyloxy, wherein in case of $C_3$-$C_{12}$ alkyloxy both carbon atoms in α- and β-position next to the oxygen are not branched;
$X_1$ is $C_2$-$C_8$ alkylene; or
$R_7$ is a group of formula V or hydrogen;
$R_{10}$ is a group of formula VI or hydrogen;
$R_{13}$ is a group of formula VII or hydrogen;
$R_8$, $R_9$, $R_{11}$, $R_{12}$, $R_{14}$ and $R_{15}$ are each independently from each other $C_1$-$C_{12}$ alkyl;
$Z_5$, $Z_6$, $Z_7$, $Z_8$, $Z_9$, $Z_{10}$, $Z_{13}$, $Z_{14}$ and $Z_{15}$ are each independently from each other $C_1$-$C_{12}$ alkyloxy, wherein in case of $C_3$-$C_{12}$ alkyloxy both carbon atoms in α- and β-position next to the oxygen are not branched;
$X_2$, $X_3$ and $X_4$ are each independently from each other $C_2$-$C_6$ alkylene.

Preferred is a compound of formula I or formula II, wherein
$R_1$ is a group of formula III or hydrogen;
$R_4$ is a group of formula IV or hydrogen;
$R_2$, $R_3$, $R_5$ and $R_6$ are each independently from each other $C_1$-$C_{12}$ alkyl;
$Z_1$, $Z_2$, $Z_3$, $Z_4$, $Z_{11}$ and $Z_{12}$ are each independently from each other linear $C_1$-$C_2$ alkyloxy;
$X_1$ is $C_2$—Ca alkylene; or
$R_7$ is a group of formula V or hydrogen;
$R_{10}$ is a group of formula VI or hydrogen;
$R_{13}$ is a group of formula VII or hydrogen;
$R_8$, $R_9$, $R_{11}$, $R_{12}$, $R_{14}$ and $R_{15}$ are each independently from each other $C_1$-$C_{12}$ alkyl;
$Z_5$, $Z_6$, $Z_7$, $Z_8$, $Z_9$, $Z_{10}$, $Z_{13}$, $Z_{14}$ and $Z_{15}$ are each independently from each other linear $C_1$-$C_{12}$ alkyloxy;
$X_2$, $X_3$ and $X_4$ are each independently from each other $C_2$-$C_6$ alkylene.

Preferred is a compound of formula I or formula II, wherein
$R_1$ is a group of formula III and $R_4$ is a group of formula IV,
$R_2$, $R_3$, $R_5$ and $R_6$ are butyl,
$Z_1$, $Z_2$, $Z_3$, $Z_4$, $Z_{11}$ and $Z_{12}$ are methyloxy, ethyloxy, n-propyloxy or n-undecyloxy,
$X_1$ is hexamethylene; or
$R_7$ is a group of formula V, $R_{10}$ is a group of formula VI and $R_{13}$ is a group of formula VII,
$R_8$, $R_9$, $R_{11}$, $R_{12}$, $R_{13}$ and $R_{15}$ are butyl,
$Z_5$, $Z_6$, $Z_7$, $Z_8$, $Z_9$, $Z_{10}$, $Z_{13}$, $Z_{14}$ and $Z_{15}$ are methyloxy, ethyloxy, n-propyloxy or n-undecyloxy,
$X_2$, $X_3$ and $X_4$ are ethylene.

Preferred is the compound P-201, P-202, P-203 or P-204.
The compounds are depicted below.

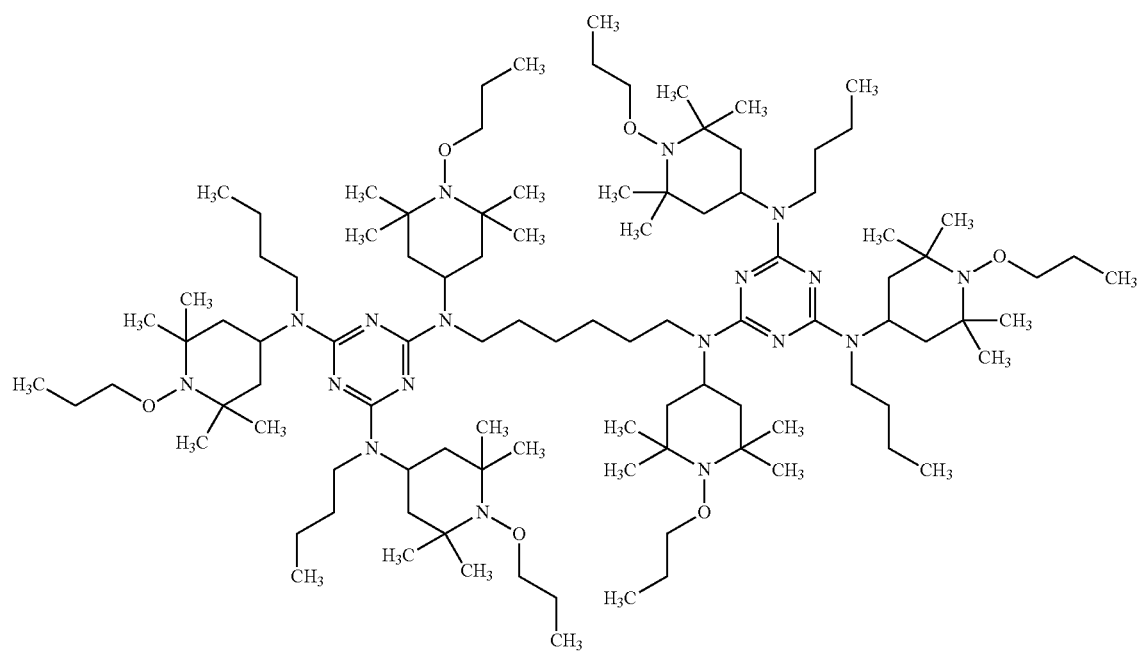

(P-201)

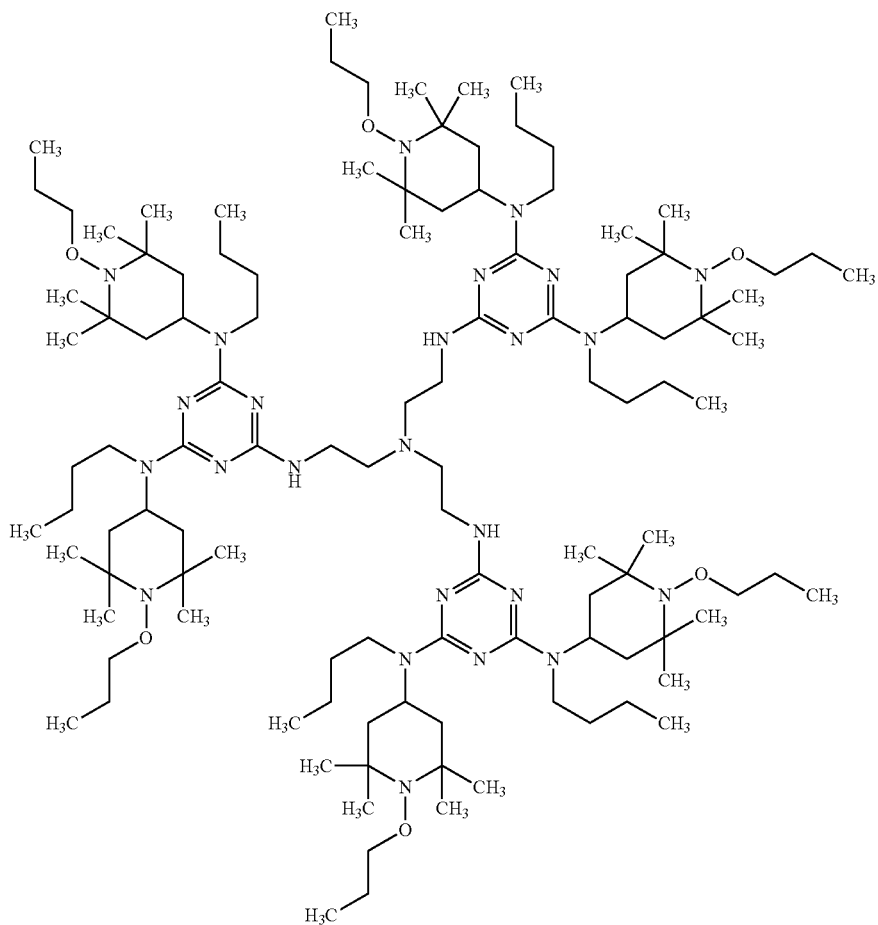
(P-202)

-continued
(P-203)
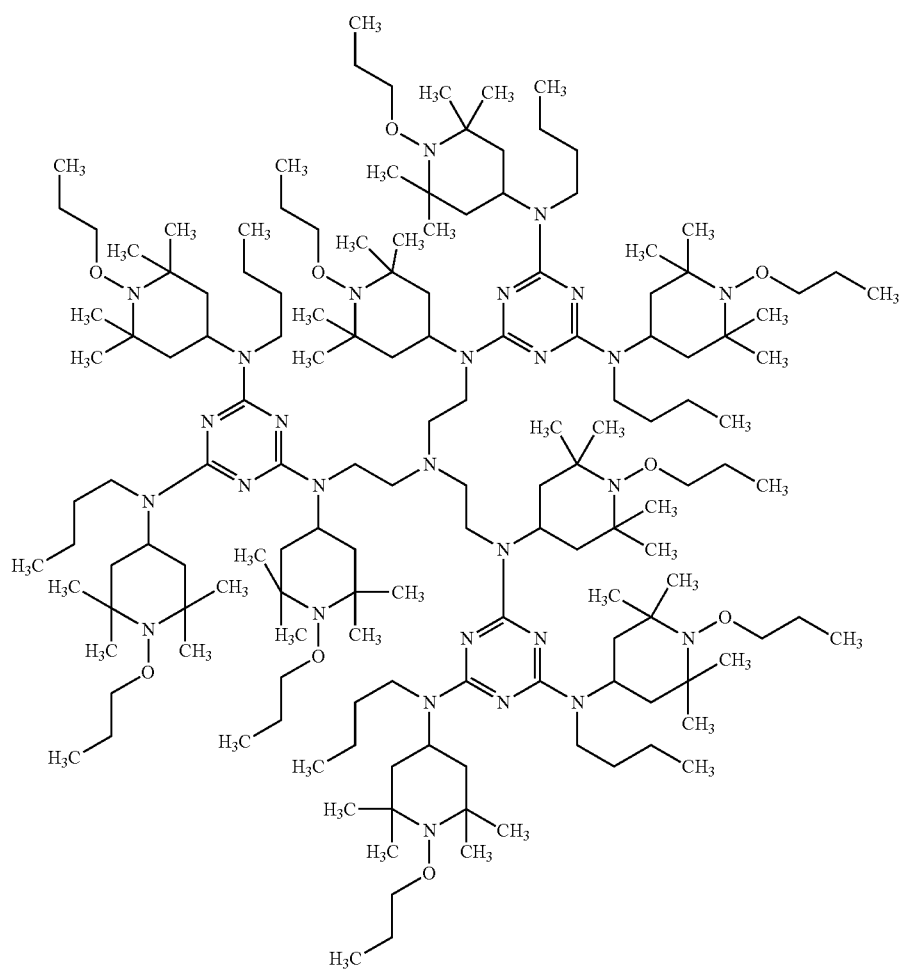
(P-204)
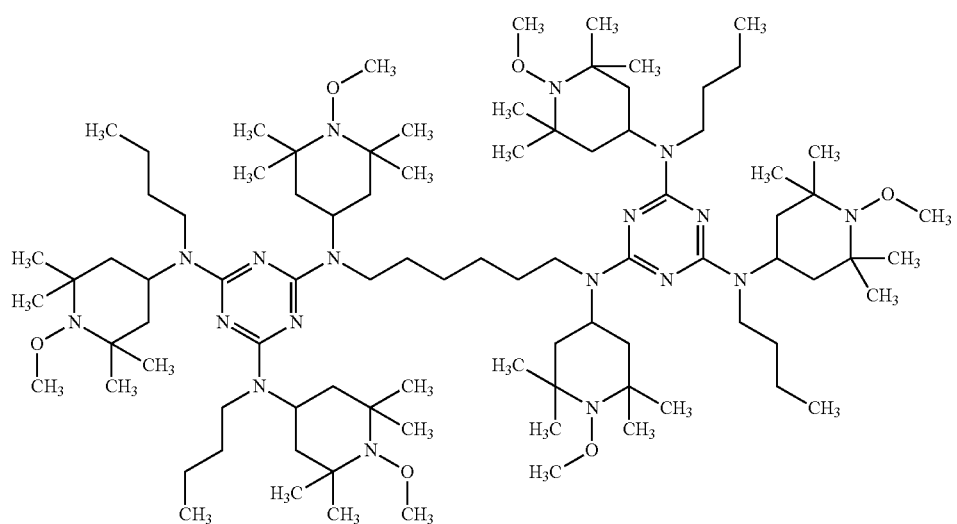

A further embodiment of this invention is a composition comprising
  a) an organic material which is susceptible to oxidative, thermal or light-induced degradation; and
  b) at least one compound of the formula I or formula II.
For example, an organic material comprises natural, semi-natural and synthetic polymers.

Examples for polymers are:
1. Polymers of monoolefins and diolefins, for example polypropylene, polyisobutylene, poly-but-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).
2. Mixtures of the polymers mentioned under 1., for example mixtures of polypropylene with polyisobutylene, polypropylene with polyethylene (for example PP/HDPE, PP/LDPE) and mixtures of different types of polyethylene (for example LDPE/HDPE).
3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is gene-rated in-situ; propylene/butadiene copolymers, isobutylene/isoprene copolymers, ethylene/vi-nylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1. above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.
4. Hydrocarbon resins (for example $C_5$-$C_9$) including hydrogenated modifications thereof (e.g. tackifiers) and mixtures of polyalkylenes and starch.

Homopolymers and copolymers from 1.-4. may have any stereostructure including syndiotactic, isotactic, hemi-isotactic or atactic; where atactic polymers are preferred. Stereoblock polymers are also included.
5. Polystyrene, poly(p-methyl styrene), poly(α-methylstyrene).
6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.
6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrenelethylene/propylene/styrene.
6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).
6c. Hydrogenated aromatic polymers derived from hydrogenation of polymers mentioned under 6a.

Homopolymers and copolymers may have any stereostructure including syndiotactic, isotactic, hemi-isotactic or atactic; where atactic polymers are preferred. Stereoblock polymers are also included.
7. Graft copolymers of vinyl aromatic monomers such as styrene or α-methylstyrene, for example styrene on polybutadiene, styrene on polybutadiene-styrene or polybutadiene-acry-lonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloridelvinylidene chloride, vinyl chloride/vinyl acetate or vinylidene chloride/vinyl acetate copolymers.

9. Polymers derived from α,β-unsaturated acids and derivatives thereof such as polyacry-lates and polymethacry-lates; polymethyl methacrylates, polyacrylamides and polyacryloni-triles, impact-modified with butyl acrylate.

10. Copolymers of the monomers mentioned under 9. with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or ace-tals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1. above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadi-enes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an ela-stomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydan-toins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, poly-buty-leneadipate/terephthalate, polytetramethyleneadipate/terephthalate, polybutylensuccinate/-adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term 'polylactic acid (PLA)' designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydr-oxy-valeric acid, 6-hydroxy-caproic acid and cyclic forms thereof; the terms 'lactic acid' or 'lactide' include L-lactic acid, D-lactic acid, mixtures and dimers thereof, i.e. L-lactide, D-lactide, meso-lacide and any mixtures thereof.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Poly-amide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

A coating binder is for example an acid catalyzed two component system or an air drying system.

A preferred polymer for component a) is a thermoplastic polymer or a coating binder.

In particular, component a) is a thermoplastic polymer. Of high relevance is the group of thermoplastic polyolefins, especially homo- or copolymers containing polymerized propylene or ethylene. Especially preferred is polypropylene or polyethylene, very particular polyethylene.

Preferred as component a) are also biodegradable polymers of either natural or synthetic origin.

Examples are polyethylensuccinate (Lunare SE (RTM, Nihon Shokubai)), polybutylensuccinate (Bionolle 1000 (RTM, Showa Highpolymer)), polybutylensuccinate/adipate (Bionolle 3000 (RTM, Showa Highpolymer)), polybutylensuccinate/carbonate (lupec (RTM, Mitsubishi Gas Chemicals)), polybutylensuccinate/terephtalate (Biomax (RTM, Dupont), Ecoflex (RTM, BASF), EasterBio (RTM, Eastman Chemicals)), polycaprolactone (CelGreen PH (RTM, Daicel Kagaku), Tone (RTM, UCC)), poly(hydroxyalkanoates) (Nodax (RTM, Procter and Gamble), from Metabolix), poly-3-hydroxybutyrate (Biogreen (RTM, Mitsubishi Gas Chemicals)), polylactic acid (NatureWorks (RTM, Cargill), LACEA (RTM, Mitsui Chemicals), Lacty (RTM, Shimadzu Seisakusho)), polyester amides or blends of these materials with natural or modified starch, polysaccharides, lignin, wood flour, cellulose and chitin.

The employed amount of component b) in regard to component a) varies with the particular organic material and the selected application.

In general, the component b) of the present invention is employed from about 0.01 to about 10% by weight of the component a).

An advantageous range is from 0.05 to 5%, in particular 0.05% to 3%. Especially preferred is 0.1% to 1%.

Another advantageous range is, in particular for improving flame retardancy, from 0.6% to 3%, especially from 0.7% to 1.5%.

The composition as described above comprising component a) and component b) may contain further additives.

Examples of further additives are given below:

1. Antioxidants
1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butyl-phenol, 2,6-di-tert-bu-tyl-4-isobutylphenol, 2,6-dicyclopentyl-4-methylphenol, 2-(a-methylcyclohexyl)-4,6-dimethyl-phenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols, for example 2,4-dioctylthiomethyl-6-tert-butylphenol, 2,4-dioctyl-thiomethyl-6-methylphenol, 2,4-dioctylthiomethyl-6-ethylphenol, 2,6-di-dodecylthiomethyl-4-nonylphenol.
1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-bu-tyl-4-hydroxyanisole, 3,5-di-tert-butyl-4-hydroxyphenyl stearate, bis(3,5-di-tert-butyl-4-hydroxyphenyl) adipate.
1.4. Tocopherols, for example α-tocopherol, β-tocopherol, γ-tocopherol, δ-tocopherol and mixtures thereof (vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.
1.7. O-, N- and S-benzyl compounds, for example 3,5,3',5'-tetra-tert-butyl-4,4'-dihydroxydi-benzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.
1.8. Hydroxybenzylated malonates, for example dioctadecyl-2,2-bis(3,5-di-tert-butyl-2-hy-droxybenzyl)malonate, di-octadecyl-2-(3-tert-butyl-4-hydroxy-5-methylbenzyl) malonate, di-dodecylmercaptoethyl-2,2-bis (3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.
1.9. Aromatic hydroxybenzyl compounds, for example 1,3,5-tris(3,5-di-tert-butyl-4-hydroxy-benzyl)-2,4,6-trimethylbenzene, 1,4-bis(3,5-di-tert-butyl-4-hydroxybenzyl)-2,3,5,6-tetrame-thylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxyben-zyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxy-phenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hy-droxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, for example with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid, for example N,N-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpro-pionyl)hydrazide, N,N'-bis[2-(3-[3,5-di-tert-butyl-4-hydroxyphenyl]propionyloxy)ethyl]oxamide (Naugard XL-1, (RTM, supplied by Uniroyal).

1.18. Ascorbic acid (vitamin C)

1.19. Aminic antioxidants, for example N,N'-di-isopropyl-p-phenylenediamine, N,N'-di-sec-bu-tyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicy-clohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phe-nyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenyl-amines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N,N'-tetraphenyl-1,4-diaminobut-2-ene.

2. UV absorbers and light stabilizers 2.1. 2-(2'-Hydroxypohenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphe-nyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyl-oxy)-carbonylethyl]-2'-hydroxyphenyl)-5-chloro-benzotriazole, 2-(3'-tert-butyl-2'-hydroxy-5'-(2- methoxycarbonylethyl)phenyl)-5-chloro-benzotriazole, 2-(3'-tert-butyl-2'-hydroxy-5'-(2-meth-oxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-iso-octyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-bu-tyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-($\alpha,\alpha$-dimethylbenzyl)-5'-(1,1,3,3-tetramethylbutyl)-phenyl]-benzotriazole; 2-[2'-hydroxy-3'-(1,1,3,3-tetramethylbutyl)-5'-($\alpha,\alpha$-dimethylbenzyl)-phenyl]benzotriazole.

2.2. 2-Hydroxybenzophenones, for example the 4-hydroxy, 4-methoxy, 4-octyloxy, 4-decyl-oxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylben-zoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinna-mate, butyl $\alpha$-cyano-$\beta$-methyl-p-methoxycinnamate, methyl $\alpha$-carbomethoxy-p-methoxycin-namate, N-($\beta$-carbomethoxy-$\beta$-cyanovinyl)-2-methylindoline, neopentyl tetra($\alpha$-cyano-$\beta,\beta$-diphenylacrylate.

2.5. Nickel compounds, for example nickel complexes of 2,2'-thio-bis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphe-nylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-$\alpha$-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)-oxymethyl-3,3,5-trimethyl-2-morpholinone, Sanduvor (RTM, Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4- dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyl-oyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristea-ryl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyl-dibenz[d,g]-1,3,2-dioxaphosphocin, 2,2',2''-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:
Tris(2,4-di-tert-butylphenyl) phosphite (Irgafos 168 (RTM, Ciba Inc.), tris(nonylphenyl) phosphite,

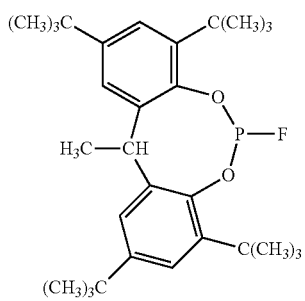

(A)

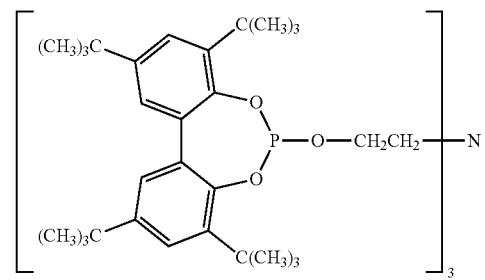

(B)

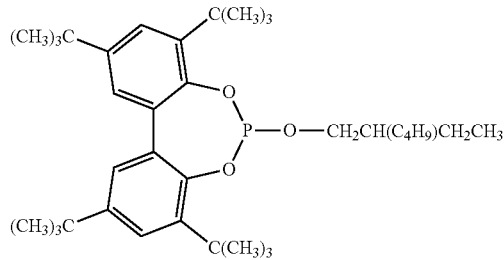

(C)

(D)

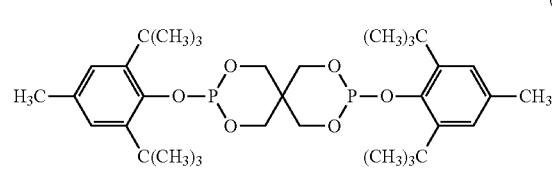

(E)

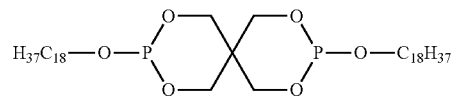

(F)

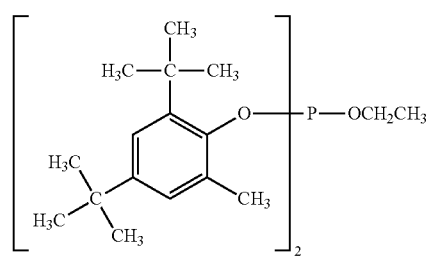

(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-α-phenylnitrone, N-ethyl-α-methylnitrone, N-octyl-α-heptylnitrone, N-lauryl-α-undecylnitrone, N-tetradecyl-α-tridecylnitrone, N-hexadecyl-α-pentadecylnitrone, N-octadecyl-α-heptadecylnitrone, N-hexadecyl-α-heptadecylnitrone, N-octadecyl-α-pentadecylnitrone, N-heptadecyl-α-heptadecylnitrone, N-octadecyl-α-hexa-decylnitrone, nitrone derived from N,N-dialkylhydroxylamine derived from hydrogenated tallow amine.
7. Thiosynergists, for example dilauryl thiodipropionate, dimistryl thiodipropionate, distearyl thiodipropionate or distearyl disulfide.
8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis-(β-dodecylmercapto)propionate.
9. Polyamide stabilizers, for example copper salts in combination with iodides and/or phosphorus compounds and salts of divalent manganese.
10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.
11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers), or Irga-clear XT 386 (RTM, Ciba). Especially preferred are 1,3:2,4-bis(3',4'-dimethylbenzylidene)-sorbitol, 1,3:2,4-di(paramethyldibenzylidene)sorbitol, and 1,3:2,4-di(benzylidene)sorbitol.
12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.
13. Other additives, for example pigments, such as carbon black, titanium dioxide in its rutile or anatase forms, color pigments; plasticisers; lubricants; emulsifiers; rheology additives; antislip/antiblock additives; catalysts; flow-control agents; optical brighteners; antistatic agents and blowing agents.
14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-d i-tert-butyl-3-[4-(2-stearoyloxy-ethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctyl-benzofuran-2-one.
15. Terpene derivatives, for example those disclosed in WO 2003/080011, those mentioned in the comprehensive list of Kirk-Othmer, Encyclopedia of Chemical Technology, John Wiley & Sons, 4$^{th}$ edition (1994), Vol. 23, p. 833-882.
16. Flame retardants
16.1 phosphorus containing flame retardants, for example tetraphenyl resorcinol diphosphite (Fyrolflex RDP, RTM, Akzo Nobel), tetrakis(hydroxymethyl)phosphonium sulphide, triphenyl phosphate, diethyl-N,N-bis(2-hydroxyethyl)-aminomethyl phosphonate, hydroxyalkyl esters of phosphorus acids, ammonium polyphosphate (APP), resorcinol diphosphate oligomer (RDP), phosphazene flame retardants or ethylenediamine diphosphate (EDAP).
16.2 nitrogen containing flame retardants, for example melamine-based flame retardants, isocyanurates, polyisocyanurate, esters of isocyanuric acid, like tris-(2-hydroxyethyl)isocyanurate, tris(hydroxymethyl)isocyanurate, tris (3-hydroxy-n-propyl)isocyanurate, triglycidyl isocyanurate, melamine cyanurate, melamine borate, melamine phosphate, melamine pyrophosphate, melamine polyphosphate, melamine ammonium polyphosphate, melamine ammonium pyrophosphate, dimelamine phosphate, dimelamine pyrophosphate, benzoguan-amine, allantoin, glycoluril, urea cyanurate, a condensation product of melamine from the series melem, melam, melon and/or a higher condensed compound or a reaction product of melamine with phosphoric acid or a mixture thereof.
16.3 organohalogen flame retardants, for example polybrominated diphenyl oxide (DE-60F, Great Lakes), decabromodiphenyl oxide (DBDPO; Saytex 102E (RTM, Albemarle)), tris[3-bromo-2,2-bis(bromomethyl)propyl] phosphate (PB 370, (RTM, FMC Corp.)), tris(2,3-dibromopropyl)phosphate, tris(2,3-dichloropropyl) phosphate, chlorendic acid, tetrachloro-phthalic acid, tetrabromophthalic acid, poly-β-chloroethyl triphosphonate mixture, tetrabromobisphenol A-bis(2,3-dibromopropyl ether) (PE68), brominated epoxy resin, ethylene-bis(tetrabromophthalimide) (Saytex BT-93 (RTM, Albemarle)), bis(hexachlorocyclopentadieno) cyclooctane (Declorane Plus (RTM, Oxychem)), chlorinated paraffins, octabromodiphenyl ether, hexachlorocyclopentadiene derivatives, 1,2-bis(tribromophenoxy)ethane (FF680), tetrabromobisphenol A (Saytex RB100 (RTM, Albemarle)), ethylene bis-(dibromonorbornane-dicarboximide) (Saytex BN-451 (RTM, Albemarle)), bis-(hexachlorocyloentadeno)cyclooctane, PTFE, tris (2,3-dibromopropyl) isocyanurate or ethylene-bis-tetrabromophthalimide. The halogenated flame retardants mentioned above are routinely combined with an inorganic oxide synergist.
16.4 inorganic flame retardants, for example aluminium trihydroxide (ATH), boehmite (AlOOH), magnesium dihydroxide (MDH), zinc borates, $CaCO_3$, organically modified layered silicates, organically modified layered double hydroxides, and mixtures thereof. In regard to the synergistic combination with halogenated flame retardants, the most common inorganic oxide synergists are zinc oxides, antimony oxides like $Sb_2O_3$ or $Sb_2O_5$ or boron compounds.

Preferred is a further additive selected from the group of antioxidants, UV absorbers, hindered amine light stabilizers, nickel compounds, metal deactivators, phosphites and phosphonites, hydroxylamines, thiosynergists, nucleating agents, peroxide scavengers, fillers or reinforcing agents and terpene derivatives.

Especially preferred is a composition which comprises components a), b), a metal oxide and a phenolic antioxidant selected from the lists 1.1-1.18 as provided above. An especially preferred metal oxide in such a combination is zinc oxide.

Particularly preferred is a composition which comprises components a), b) and a phenolic antioxidant selected from the lists 1.1-1.18 as provided above.

Very preferred phenolic antioxidants in these compositions are esters of β-(3,5-di-tert-butyl-4-hydroxyphenyl)propionic acid with mono- or polyhydric alcohols (i.e. list 1.13.). Especially preferred are tetrakis-[3-(3,5-di-tert-butyl-4-hydroxy-phenyl)-propionyloxymethyl]-methane and 3-(3, 5-di-tert-butyl-4-hydroxy-phenyl)-propionic acid octadecyl ester.

Preferred is is a composition which comprises components a), b), a phenolic antioxidant selected from the lists 1.1-1.18 as provided above, a phosphite stabilizer selected from the list 4 as provided above and a basic costabilizer selected from the list 10 as provided above. Especially preferred is the composition, wherein said basic costabilizer is calcium stearate.

Preferred is a further additive selected from the group of flame retardants comprising phosphorus containing flame retardants, nitrogen containing flame retardants, halogenated flame-retardants and inorganic flame retardants.

The optional further additive in the stabilized compositions of the invention may be contained from 0.01% to 5%, preferably from 0.025% to 2%, and especially from 0.1% to 1% by weight of the stabilized composition.

In case of a flame retardant as optional further additive, the flame retardant is advantageously contained in the composition of the invention in an amount from 0.5% to 60.0% by weight of the organic material; for instance from 1.0% to 40.0%; for example from 5.0% to 35.0% by weight of the organic material.

The component b) as well as an optional further additive of the invention may readily be incorporated into the organic material as component a) by conventional techniques, at any convenient stage prior to the manufacture of shaped articles therefrom.

The component b) as well as an optional further additive can judiciously be incorporated by one of the following methods:

as emulsion or dispersion (e.g. to latices or emulsion polymers)

as a dry mixture during the blending by direct introduction into the processing apparatus (e.g. extruders, internal mixers)

as solution in an organic solvent as melt.

The organic material as component a) can be in the form of a solid, solution, suspension or emulsion.

Incorporation of the component b) as well as an optional further additive is in case of thermoplastic polymers as component a) performed best in a thermal compounding step. Thorough blending of the component a), component b) as well as an optional further additive is followed by an extrusion of the physical blend at elevated temperature. Typically an extruder with suitable screw configuration is used for this step.

The additives can also be added to the polymer as component a) in the form of a masterbatch ('concentrate'), which contains the component b) as well as an optional further additive incorporated in a further polymer of the masterbatch. The concentration for the additives is, for example, from 1% to 40%, in particular 2.5% to 25% by weight of the masterbatch. Said further masterbatch polymer must not be necessarily of identical structure than the polymer as component a). The masterbatch polymer can be produced in a different manner to that of the polymer as component a). The masterbatch can be in the form of a powder, granules, solutions, suspensions or in the form of latices.

In case of a polymer as component a), the polymer compositions of this invention can be employed in various forms and/or processed to give various final products, for example as to obtain films, fibres, tapes, moulding compositions, profiles or as binders for coating materials, adhesives or putties.

In more detail, the final product respectively article can be any type of polymeric article, which needs stabilization in natural sunlight and/or humidity at low, ambient or elevated temperature. For example, the polymer component may be used to manufacture polymeric films, sheets, bags, bottles, styrofoam cups, plates, utensils, blister packages, boxes, package wrappings, plastic fibers, tapes, agricultural articles such as twine agricultural films, mulch films, small tunnel films, banana bags, direct covers, nonwoven, pots for agricultural use, goetextiles, landfill covers, industrial covers, waste covers, temporary scaffolding sheets, building films, silt fences, poultry curtains, films for building temporary shelter constructions, disposable diapers, disposable garments or the like.

The polymeric articles may be manufactured by any process available to those of ordinary skill in the art including, but not limited to, extrusion, extrusion blowing, film casting, film blowing, calendering, injection molding, blow molding, compression molding, thermoforming, spinning, blow extrusion or rotational casting.

For the production of the desired polymeric article out of the polymer compositions of this invention, any appropriate equipment can be used, depending on the final form of the article, for example a blow extruder in the case of films, an extrusion machine in the case of sheets or an injection molding machine.

A further embodiment of this invention is a method for stabilization of an organic material susceptible to oxidative, thermal or light-induced degradation, which comprises the incorporation therein or applying thereto a compound of formula I or formula II. Preferred is also the use of a compound of formula I or formula II for stabilization of an organic material susceptible to oxidative, thermal or light-induced degradation.

A further embodiment of this invention is a method for improving flame retardancy of an organic material, which comprises the incorporation therein or applying thereto a compound of formula I or formula II.

Preferred is also the use of a compound of formula I or formula II for improving the flame retardancy of an organic material.

All definitions and preferences stated above apply equally for all embodiments of this invention.

Another aspect of this invention is the intermediate N-(2, 2,6,6-tetramethyl-1-propoxy-piperidin-4-yl)-N',N'-bis-[2-(2,2,6,6-tetramethyl-1-propoxy-piperidin-4-ylamino)-ethyl]-ethane-1,2-diamine.

The compounds of formula I or formula II can be prepared according to known methods.

Some of the methods are exemplified in the synthetic example. Furthermore, the referred literature therein provides further synthetic approaches.

SYNTHETIC EXAMPLES

All chemicals are used as received and not purified prior to synthesis. All reactions are carried out under nitrogen atmosphere except when otherwise stated.

Example 1

N,N-Bis-(2,2,6,6-tetramethyl-piperidin-4-yl)-N,N'-bis-{2,4-bis-{n-butyl-(2,2,6,6-tetramethyl-piperidin-4-yl)-amino}-[1,3,5]triazin-6-yl}-hexane-1,6-diamine (I-101)

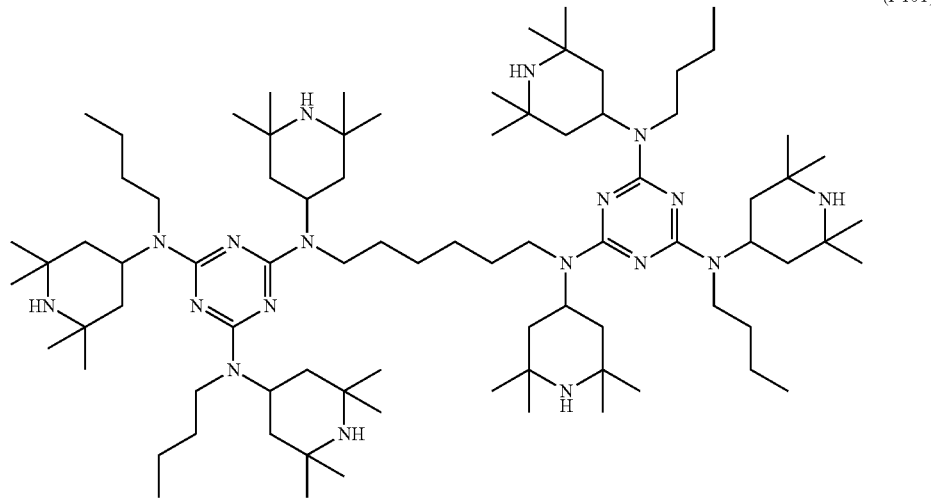

(I-101)

a) Compound I-101 is disclosed in 'Rearrangement of the polymer structure in the presence of high molecular weight additives', A. P. Marin, V. Borzatta, L. Greci, Journal of Macromolecular Science, Pure and Applied Chemistry, 1998, A35(7&8), pages 1299-1311.

b) A four-necked round-bottom flask equipped with a mechanical stirrer, thermocouple, dropping funnel and condenser is charged with 100.0 g (0.542 mol) of cyanuric chloride suspended in 300 mL of toluene and 70 g of $NaOH_{aq}$ (30%; 1.75 mol). To this suspension by means of a dropping funnel is added 233 g (1.10 mol) of N-butyl triacetonediamine dissolved in 50 mL of toluene. The mixture was heated under stirring at 70° C. for one hour then cooled down to room temperature.

71.4 g (0.181 mol) of N,N'-bis-(2,2,6,6-tetramethylpiperidin-4-yl)-hexane-1,6-diamine in 50 mL of toluene is added to the reaction mixture over 30 minutes. Then, the reaction is refluxed overnight and finally cooled down to $^1$H-NMR to reveal that the major part of the chloride atoms added to the reaction mixture over 30 minutes. Then, the reaction is refluxed overnight and finally cooled down to room temperature. The organic phase is washed with 300 mL of $H_2O$, dried over $Na_2SO_4$ and concentrated undervacuum. The crude brown-yellow residue is analyzed by of the original cyanuric chloride unit have reacted to result in compound I-101. The residue is purified by dissolving in 350 mL of refluxing acetone and afterwards precipitation in the refrigerator at −20° C. overnight.

Yield: 260 g (69%)

TGA (10° C./min): 260° C.: −0.06%; 280° C.: −0.09%; 300° C.: −0.18%

Melting point: 188-190° C.

Elemental analysis: calculated C: 70.64% H: 11.28% N: 18.08% found C: 70.21% H: 11.21% N: 17.99%

Example 2

N,N'-Bis-(2,2,6,6-tetramethyl-1-propoxy-piperidin-4-yl)-N,N'-bis-{2,4-bis-{n-butyl-(2,2,6,6-tetramethyl-1-propoxy-piperidin-4-yl)-amino}-[1,3,5]triazin-6-yl}-hexane-1,6-diamine (P-201)

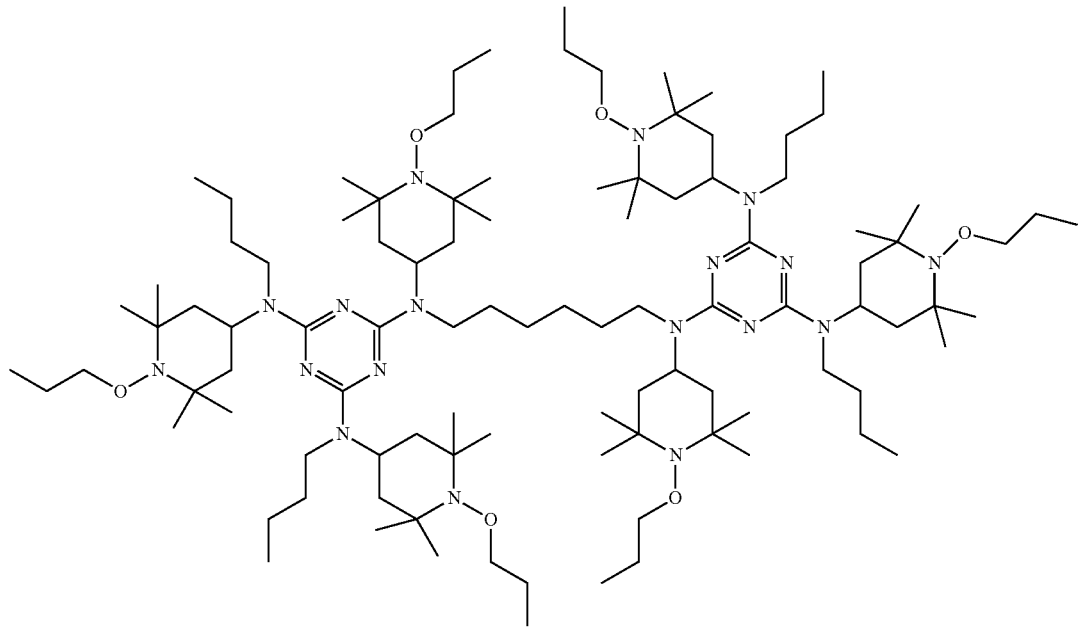

(P-201)

In a 1.0 L autoclave equipped with a mechanical stirrer are added 100 g (0.0717 mol) of compound I-101, 91.4 g (0.755 mol) of allyl bromide and 104.1 g (0.754 mol) of $K_2CO_3$, suspended in 500 mL of toluene. The mixture is heated at 160° C. overnight, cooled down and washed with 300 mL of $H_2O$ at 50° C. Toluene is removed under reduce pressure to give a yellow solid. This solid is placed in a four-necked round-bottom flask equipped with a mechanical stirrer, thermocouple and a dropping funnel. 500 mL of $CH_2Cl_2$ and 110 g (0.797 mol) of $K_2CO_3$ are also charged in the flask. The solution is cooled down to 00° C. and 90 g of peracetic acid (35%; 0.414 mol) is slowly added over 30 minutes. Afterwards, the mixture is warmed up and stirred at room temperature for one day. 1.0 L of $H_2O$ is added. The organic phase is separated, dried over $Na_2SO_4$ and filtered. The solvent is removed to give a brown material which was loaded in a 1.0 L autoclave without further purification. 600 mL of toluene and 6.0 g of Pd/C (5%) are also loaded in the autoclave and the overall mixture is heated at 70° C. for 4 hours.

The solution is cooled to room temperature, filtered to remove the catalyst and dried under reduced pressure. The residue is dissolved in 15 mL of $CH_2Cl_2$ and then precipitated with cold methanol to give compound P-201 as white-yellow powder.

Yield: 117 g (94%)
TGA (10° C./min): 210° C.: −0.65%; 260° C.: −1.15%; 300° C.: −4.95%
Melting point: 139-143° C.
Elemental analysis: calculated C: 68.92% H: 11.10% N: 14.47%
found C: 68.40% H: 10.91% N: 14.18%

Example 3 n-Butyl-(2,2,6,6-tetramethyl-1-propoxy-piperidin-4-yl)-amine (I-102)

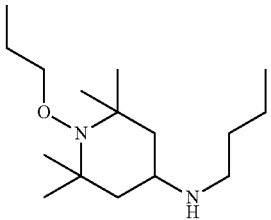

(I-102)

The synthesis of compound I-102 is performed starting from 1-propyloxy-2,2,6,6-tetramethyl-piperidin-4-one according to the procedure described in patent WO 2008/003605 A1, page 19, line 8.

Example 4

N,N'-Dibutyl-6-chloro-N,N'-bis-(2,2,6,6-tetramethyl-1-propoxy-piperidin-4-yl)-[1,3,5]triazine-2,4-diamine (I-103)

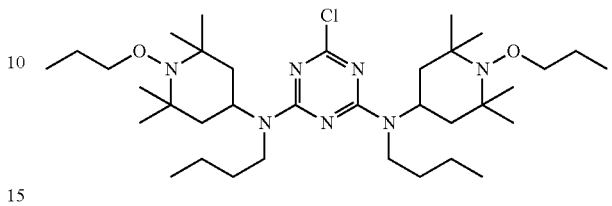

(I-103)

a) The synthesis of compound I-103 is provided as example 8 in U.S. Pat. No. 6,117,995, column 51, line 1.
b) A four-necked round-bottom flask equipped with a mechanical stirrer, thermocouple, dropping funnel and condenser is charged with 27.3 g (0.148 mol) of cyanuric chloride and 200 mL of xylene at 0-5° C. 40 g (0.148 mol) of compound I-102 in 25 mL of xylene are slowly added over 20 minutes to this solution. After 90 minutes, further 40 g (0.148 mol) of compound I-102 in 25 mL of xylene and 25 mL of water are slowly added over 20 minutes to the system allowing the temperature to reach 45° C.

The mixture is kept at 45° C. for 30 minutes. Then, 13.0 g of $NaOH_{aq}$ (30%, 0.325 mol) are slowly added over 30 minutes. The temperature is then rised to 80° C. and the reaction is heated for 2 hours at 80° C. After being cooled to room temperature, the organic phase is washed with 300 mL of water, separated and dried over $Na_2SO_4$. The solvent is removed in vacuo to obtain compound I-103 as a yellowish liquid, which solidifies in the refrigerator at a temperature around 4° C.

Yield: 75.4 g (78%)
TGA (10° C./min): 260° C.: −4.58%; 280° C.: −9.59%; 300° C.: −26.04%
Elemental analysis: calculated C: 64.44% H: 10.20% N: 15.03%
found C: 65.01% H: 10.11% N: 15.03%
LC/MS: [M]+: 652.93

Example 5

N,N-Bis-(2-{(2,4-bis-{n-butyl-(2,2,6,6-tetramethyl-1-propoxy-piperidin-4-yl)-amino}-[1,3,5]triazin-6-yl)-amino}-ethyl)-N'-(2,4-bis-{n-butyl-(2,2,6,6-tetramethyl-1-propoxy-piperidin-4-yl)-amino}-[1,3,5]triazin-6-yl)-ethane-1,2-diamine (P-202)

(P-202)

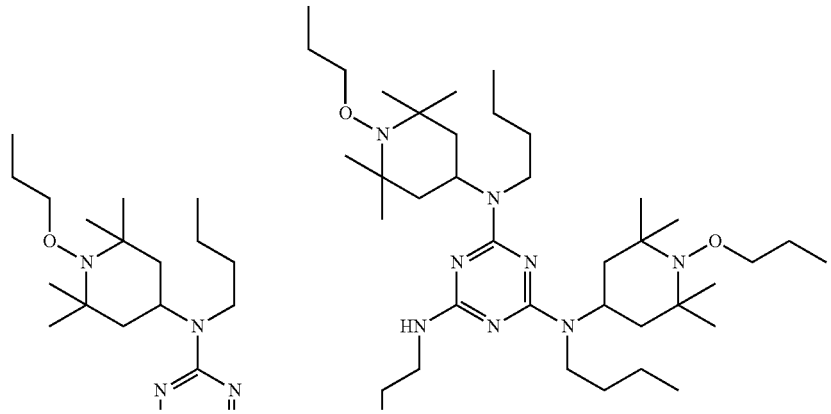

-continued

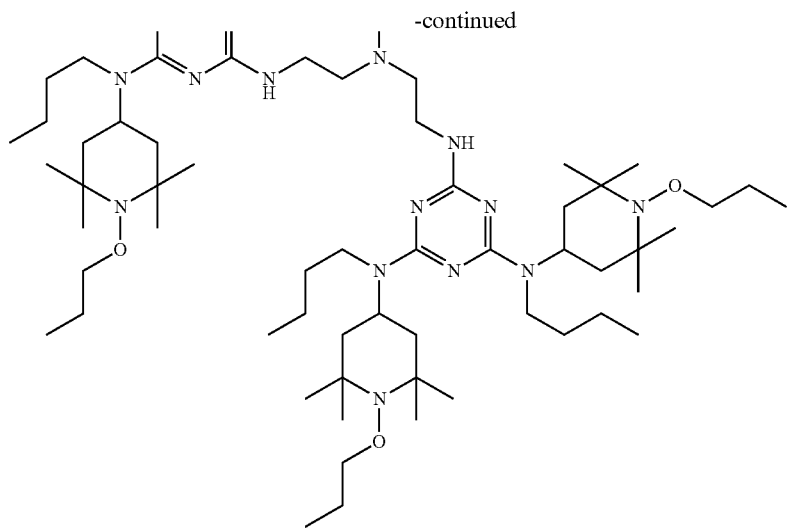

In a 1.0 L autoclave equipped with a mechanical stirrer are loaded 50 g (0.0766 mol) of compound I-103, 3.83 g (0.0262 mol) of tris(2-aminoethyl)amine and 6.5 g of NaOH$_{aq}$ (30%; 0.163 mol) in 500 mL of xylene. The mixture is heated at 160° C. for 16 hours, then cooled down and washed with 300 mL of H$_2$O at 40° C. The organic phase is separated and dried over Na$_2$SO$_4$. Evaporation of the solvent in vacuo results in a brown solid, which is purified by dissolving in 30 mL of refluxing methanol and precipitation in the refrigerator at −20° C. overnight. Compound P-202 is obtained as white powder.

Yield: 21.4 g (41%)

TGA (10° C./min): 160° C.: −0.12%; 260° C.: −1.19%; 300° C.: −9.57%

Melting point: 75-77° C.

ESI-MS (m/z) in THF/CH$_3$CN: [M]+: 1993.7, [M]$^2$+: 997.9 (MW calculated: 1994.1 g/mol)

Example 6
N-(2,2,6,6-Tetramethyl-1-propoxy-piperidin-4-yl)-N',N'-bis-[2-(2,2,6,6-tetramethyl-1-propoxy-piperidin-4-ylamino)-ethyl]-ethane-1,2-diamine (I-104)

(I-104)

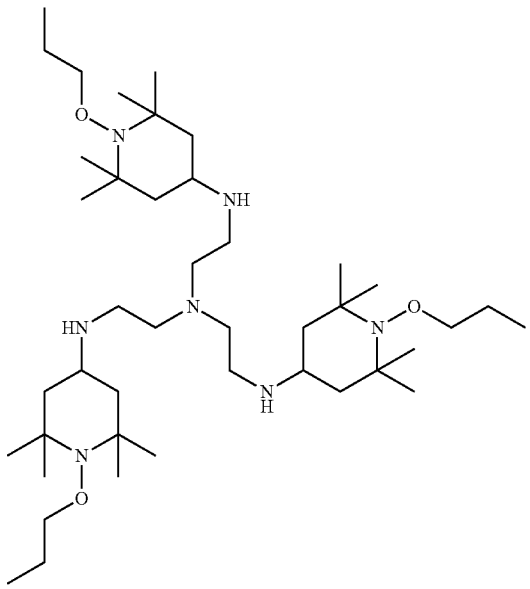

A four-necked round-bottom flask equipped with a mechanical stirrer, thermocouple, dropping funnel and condenser is charged with 30.0 g (0.141 mol) of 2,2,6,6-tetramethyl-1-propoxy-piperidin-4-one, 7.7 g (0.0526 mol) of tris-(2-aminoethyl)-amine and 350 mL of cyclohexane. The solution is heated at reflux for 3 hours and water removed. Then it is cooled to room temperature and 120 mL of MeOH are added at 15° C.

4.0 g (0.106 mol) of NaBH$_4$ is slowly added at 15° C. The solution is finally warmed up and stirred at room temperature overnight.

It is washed twice with 200 mL of H$_2$O and 200 mL of CH$_2$Cl$_2$. The solvent is removed under reduced pressure to give a yellow-orange solid. This solid is purified by sonication for 15 minutes in 120 mL of acetone to give compound I-104 as a white precipitate.

Yield: 24.5 g (63%)

TGA (10° C./min): 210° C.: −0.15%; 260° C.: −3.83%

Melting point: 126-129° C.

Elemental analysis: calculated C: 68.34% H: 11.88% N: 13.28% found: C: 67.59% H: 11.62% N: 13.08%

ESI-MS (m/z) in THF/CH$_3$CN: [M]+: 738.9 (MW calculated: 738.2 g/mol)

Example 7

N,N-Bis-(2-{(2,2,6,6-tetramethyl-1-propoxy-piperidin-4-yl)-(2,4-bis-{n-butyl-(2,2,6,6-tetramethyl-1-propoxy-piperidin-4-yl)-amino}-[1,3,5]triazin-6-yl)-amino}-ethyl)-N'-(2,2,6,6-tetramethyl-1-propoxy-piperidin-4-yl)-N'-(2,4-bis-{n-butyl-(2,2,6,6-tetramethyl-1-propoxy-piperidin-4-yl)-amino}-[1,3,5]triazin-6-yl)-ethane-1,2-diamine (P-203)

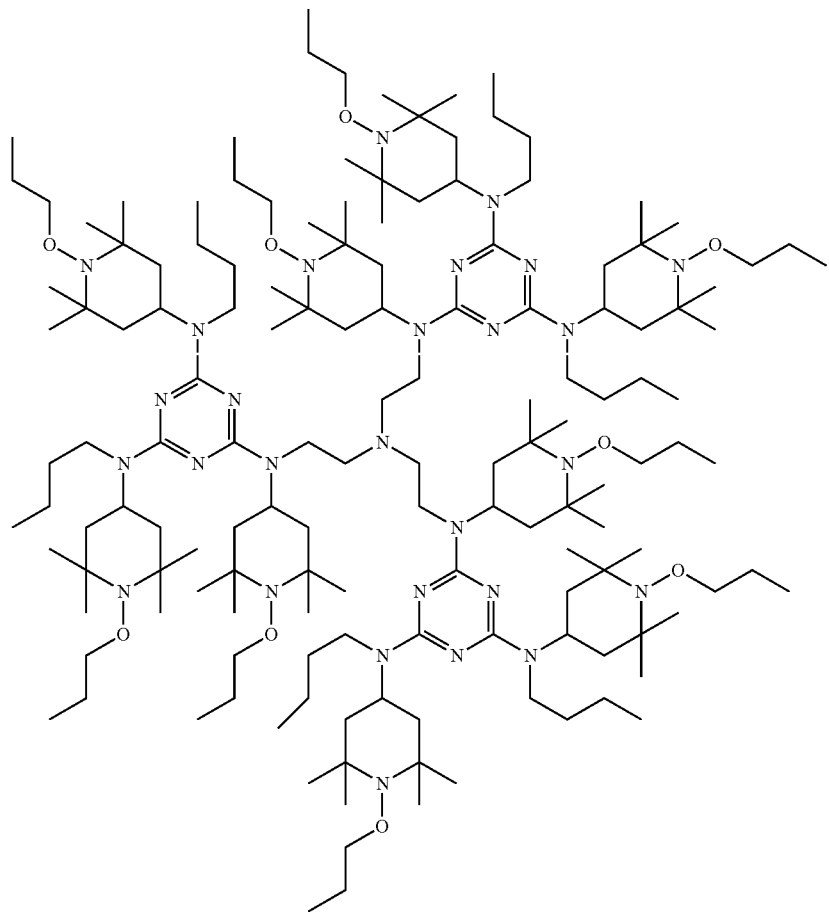

(P-203)

In a 1.0 L autoclave equipped with a mechanical stirrer are added 20.0 g (0.0271 mol) of compound I-104, 53.5 g (0.082 mol) of compound I-103 and 5.44 g of $NaOH_{aq}$ (30%; 0.136 mol) in 400 mL of xylene. The mixture is heated at 160° C. for 20 hours. The solution is cooled down and washed twice with 300 mL of $H_2O$ at 50° C. Xylene is removed under reduced pressure to give a brown solid. This solid is dissolved in 10 mL of $CH_2Cl_2$ and purified by precipitation with 250 mL of cold MeOH to give compound P-203 as a white-yellow powder.

Yield: 30.8 g (44%)
TGA (10° C./min): 210° C.: −0.07%; 260° C.: −2.96%
Melting point: 157-161° C.
ESI-MS (m/z) in $CH_2Cl_2$/MeOH: [M+MeOH]+: 2619.2 (Mw calculated: 2618.1 g/mol)
Elemental analysis: calculated C: 68.28% H: 10.99% N: 15.17%
found C: 68.19% H: 11.05% N: 15.21%

Example 8

N,N'-Bis-β-{(2,4-bis-{n-butyl-(2,2,6,6-tetramethyl-1-propoxy-piperidin-4-yl)-amino}-[1,3,5]triazin-6-yl}-amino)-propyl)-bis-N,N'-(2,4-bis-{n-butyl-(2,2,6,6-tetramethyl-1-propoxy-piperidin-4-yl)-amino}-[1,3,5]triazin-6-yl)-ethane-1,2-diamine (C-301)

a) Compound C-301 is mentioned in U.S. Pat. No. 6,117,995 (column 20, line 25).

b) A four-necked round-bottom flask equipped with a mechanical stirrer, thermocouple, dropping funnel and condenser is charged with 88.5 g (0.136 mol) of compound I-103, 5.89 g (0.0338 mol) of N,N'-bis-β-aminopropyl)-ethane-1,2-diamine and 12 g of NaOH$_{aq}$ (30%; 0.30 mol) in 300 mL of xylene. The mixture is heated at 160° C. for 24 hours, then cooled down and washed with water several times till pH=7-8.

The organic phase is separated, dried over Na$_2$SO$_4$ and the solvent removed under reduced pressure. The obtained brown-red solid is dissolved in 30 mL of CH$_2$Cl$_2$ and precipitated from 400 mL of cold MeOH to give compound C-301 as a white powder.

Yield: 28 g (31%)

TGA (10° C./min): 220° C.: −0.05%; 290° C.: −4.12%

Melting point: 102-106° C.

Maldi-Tof (m/z; α-cyano-4-hydroxycinnamic acid as matrix): [M+H]+: 2640 (MW calculated: 2638.1 g/mol)

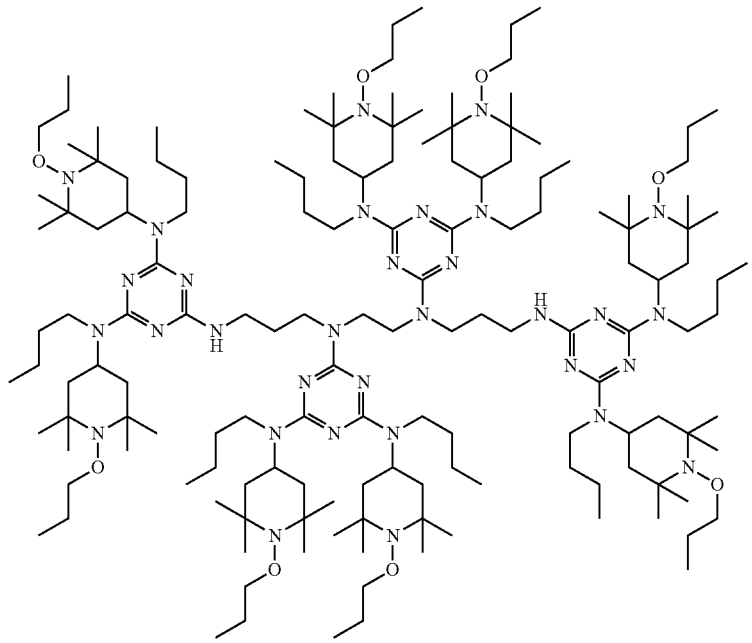

(C-301)

Elemental analysis: calculated C: 67.38% H: 10.77% N: 16.99% found C: 67.54% H: 10.91% N: 16.98%

Example 9

N,N-Bis-(2,2,6,6-tetramethyl-1-methoxy-piperidin-4-yl)-N,N'-bis-{2,4-bis-{n-butyl-(2,2,6,6-tetramethyl-1-methoxy-piperidin-4-yl)-amino}-[1,3,5]triazin-6-yl}-hexane-1,6-diamine (P-204)

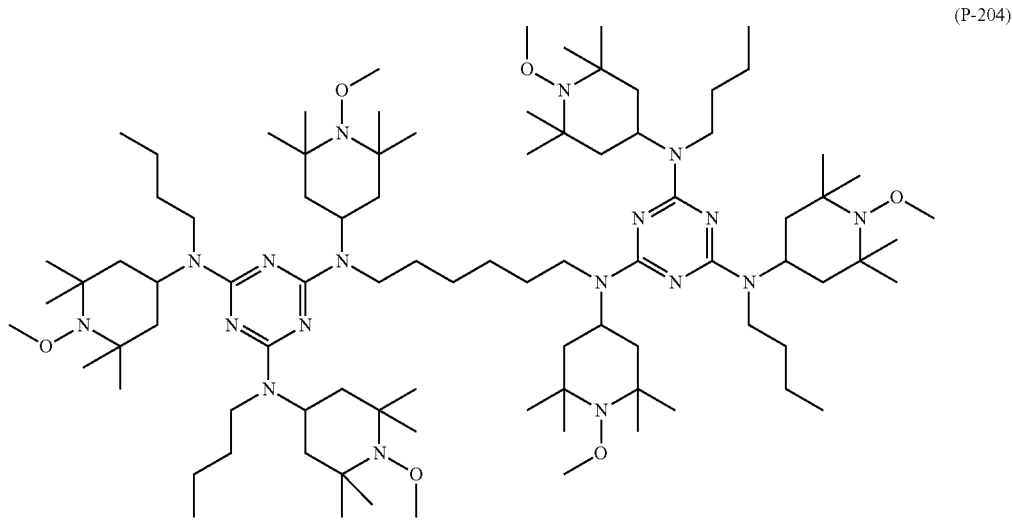

(P-204)

A 1 L reactor is charged with 150 g (0.107 mol) of compound I-101 in 275 g toluene. There are added 0.8 g (0.0024 mol) sodium tungstate dihydrate, 0.6 g (0.010 mol) acetic acid, 6.3 g (0.350 mol) water and 1.3 g benzyltrimethylammonium chloride (0.0069 mol). The reaction mass is heated to 58° C. and 213 g hydrogen peroxide (50% w/w; 3.13 mol) is added within 3 h. The reaction is stirred over night at room temperature. The reaction mass is washed with sodium carbonate solution and then with water. The obtained dark red solution is transferred to a 1.5 L reactor and 105 g toluene, 54 g water, 125 g acetic acid, 1.9 g (0.019 mol) CuCl and 120 g (2.71 mol) acetaldehyde are added. The reaction mass is heated to 40° C. and 145 g hydrogen peroxide (50% w/w; 2.13 mol) is added within 4 h followed by stirring over night. Then 0.98 g (0.0099 mol) CuCl and 60 g (1.36 mol) acetaldehyde are added. 72 g hydrogen peroxide (50% w/w; 1.07 mol) is dosed over 2 h and the reaction is stirred for 2.5 h at 40° C. Work-up: The phases are separated, the water phase is discarded. 60 g toluene is added to the organic phase and then the organic phase is washed with a solution of $Na_2CO_3$ and EDTA in water, with a solution of $Na_2CO_3$, $Na_2SO_3$ and EDTA in water and with $Na_2SO_3$ in water till no peroxides are detectable. The reaction mass is washed with sodium hydrogencarbonate solution (5% w/w) and the solvent is distilled off. The product is dried at 40-80° C. under vacuum to give compound P-204 as white to off-white powder.

Yield: 95 g $^1$H NMR (CDCl$_3$, 400 MHz, δ (ppm)): 5.4-5.0 (m); 3.67 (m); 3.29 (m); 1.9-0.8 (m)

MS (Atmospheric Pressure Chemical Ionization, m/z): 1574.1 [M+1], 1544.2, 1514.2, 1484.3

TGA (10° C./min): 210° C.: −1.68%; 260° C.: −3.31%; 300° C.: −5.99%

Melting point: 134-137° C.

Application Examples

Example 10

Light Stabilization of Low-Density Polyethylene Films

LDPE Film Manufacture:

In a turbo mixer (Caccia, Labo 10), the additives according to table 1 are mixed with LDPE (i.e. low density polyethylene). The mixture is extruded at a maximum temperature of 200° C. using an O.M.C. twin-screw extruder (model EBV 19/25, with a 19 mm screw diameter and 1:25 ratio) to granules. The granules are subsequently mixed and diluted with the same LDPE in order to obtain the calculated final concentration for preparing a 150 μm thick film, using a blow-extruder (Dolci) working at a maximum temperature of 210° C. The calculated final concentrations in the LDPE films are indicated in Table 1.

TABLE 1

| Concentration of additives employed for the LDPE film | |
|---|---|
| Film No. | Additives |
| Film 1[a] | 0.4% compound P-201 |
|  | 0.1% Irganox 1010[c] |
| Film 2[a] | 0.4% compound P-202 |
|  | 0.1% Irganox 1010[c] |
| Film 3[a] | 0.4% compound P-203 |
|  | 0.1% Irganox 1010[c] |
| Film 4[b] | 0.4% compound C-301 |
|  | 0.1% Irganox 1010[c] |
| Film 5[b] | 0.4% Tinuvin NOR 371[d] |
|  | 0.1% Irganox 1010[c] |
| Film 6[b] | 0.4% Chimassorb 2020[e] |
|  | 0.1% Irganox 1010[c] |

[a] according to the invention

[b] comparative

[c] Irganox 1010 (RTM, Ciba) is tetrakis-[3-(3,5-di-tert-butyl-4-hydroxy-phenyl)-propionyloxymethyl]-methane

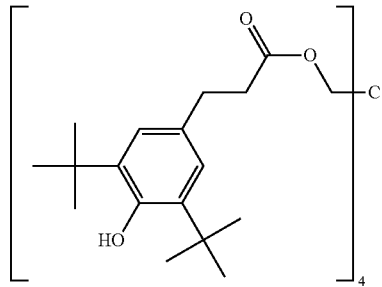

d) Tinuvin NOR 371 (RTM, Ciba) is a mixture of oligomeric compounds which are the formal condensation products of N,N'-bis-(2,2,6,6-tetramethyl-1-propoxy-piperidin-4-yl)-hexane-1,6-diamine and 2,4-dichloro-6-{n-butyl-(2,2,6,6-tetramethyl-1-propoxy-piperidin-4-yl)-amino}-[1,3,5]triazine end-capped with 2-chloro-4,6-bis-(di-n-butylamino)-[1,3,5]triazine

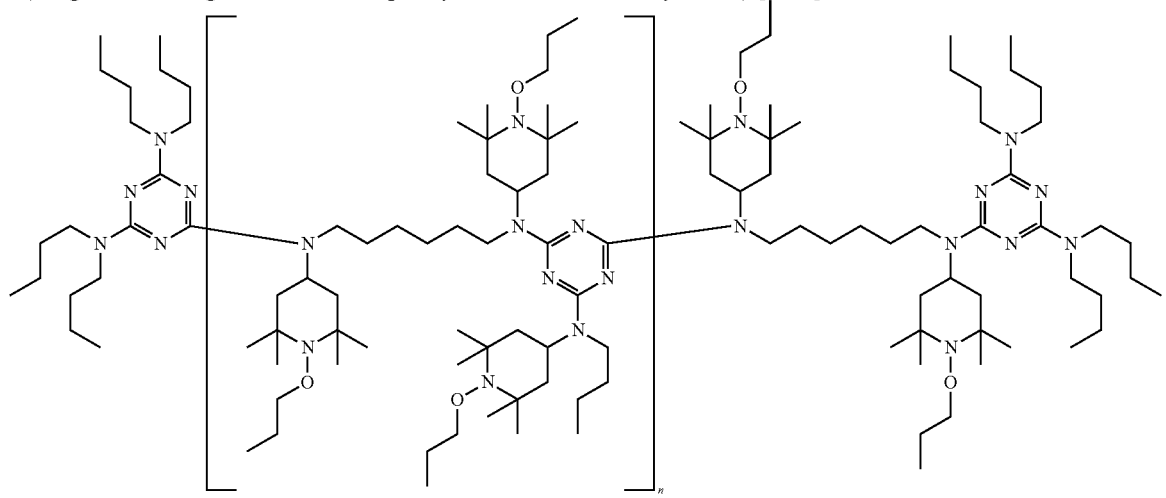

e) Chimassorb 2020 (RTM, Ciba) is a mixture of oligomeric compounds which are the formal condensation products of N,N'-bis-(2,2,6,6-tetramethyl-piperidin-4-yl)-hexane-1,6-diamine and 2,4-dichloro-6-{n-butyl-(2,2,6,6-tetramethyl-piperidin-4-yl)-amino}-[1,3,5]triazine end-capped with 2-chloro-4,6-bis-(di-n-butylamino)-[1,3,5]triazine

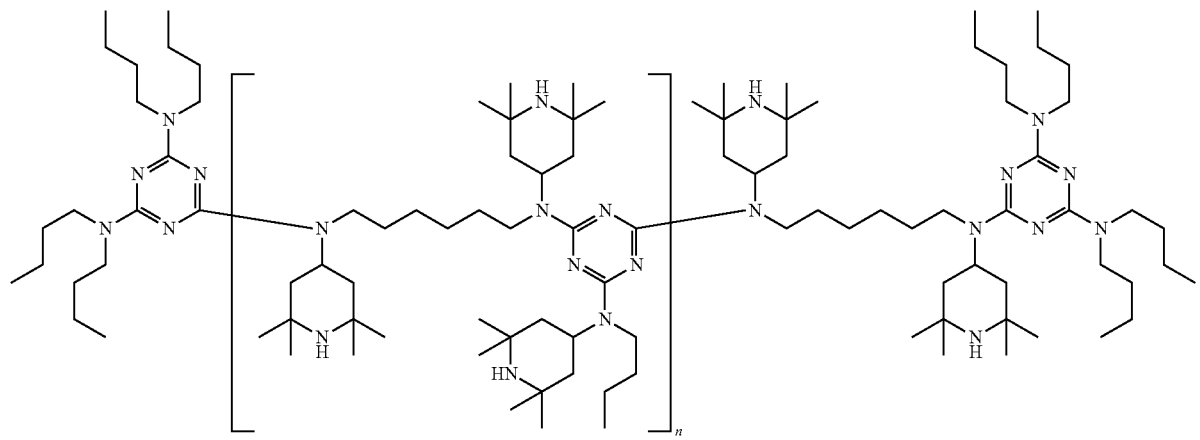

Performances of Additives as Stabilizers in LDPE Films:

Light exposure: LDPE films are exposed in an ATLAS Weatherometer (model Ci65A) equipped with a 6500 W Xenon lamp (0.35 W/m$^2$; continuous light cycle, black panel temperature=63° C.).

Vapam treatment: LDPE films are placed in a close chamber and exposed to the vapors of a 0.74 v/v aqueous solution of vapam (39.1% by weight sodium N-methyl-dithiocarbamate in water). The system is kept at 30° C. for 20 days. Then the LDPE films are subjected to light exposure as described above.

Evaluation Parameters:

1) Carbonyl increment: Evaluation of the carbonyl band increment (1710 cm-1) in LDPE films under applicative tests to assess the performances as light/heat stabilizers. A higher increment value indicates a higher degree of oxidative degradation.

2) Tensile elongation at break: Evaluation of elongation percentage property of LDPE films under applicative tests to assess the performances as light/heat stabilizers. Test carried out with ZWICK Z1.0 testing machine with a speed of 100 mm/min; a holder distance of 30 mm and at a temperature of 20° C.

A value, which is closer to the starting value for tensile elongation at break, indicates less degradation.

TABLE 2

Carbonyl increment of 150 μm additivated LDPE films upon WOM exposure

| | Time of exposure (hours) | | | | | |
|---|---|---|---|---|---|---|
| Film No. | 0 | 750 | 1300 | 2635 | 3220 | 5080 |
| Film 1[a)] | 0.000 | 0.005 | 0.007 | 0.019 | 0.024 | 0.046 |
| Film 2[a)] | 0.000 | 0.000 | 0.000 | 0.002 | 0.005 | 0.011 |

TABLE 2-continued

Carbonyl increment of 150 μm additivated LDPE films upon WOM exposure

| | Time of exposure (hours) | | | | | |
|---|---|---|---|---|---|---|
| Film No. | 0 | 750 | 1300 | 2635 | 3220 | 5080 |
| Film 5[b)] | 0.000 | 0.006 | 0.010 | 0.023 | 0.030 | 0.052 |
| Film 6[b)] | 0.000 | 0.003 | 0.006 | 0.035 | 0.043 | 0.066 |

Footnotes are listed at table 1.

TABLE 3

Tensile measurements of 150 μm additivated LDPE films upon WOM exposure

| | Time of exposure (hours) | | | | |
|---|---|---|---|---|---|
| Film No. | 0 | 1635 | 2580 | 3270 | 3996 |
| Film 1[a)] | 100 | 99 | 96 | 86 | 86 |
| Film 2[a)] | 100 | 100 | 98* | not measured | 92** |
| Film 4[b)] | 100 | not measured | 99 | 78 | 70 |
| Film 5[b)] | 100 | 99 | 94 | 88 | 80 |
| Film 6[b)] | 100 | 89 | 78 | 74 | 70 |

Footnotes are listed at table 1.
*after 2492 hours
**after 5000 hours

TABLE 4

Carbonyl increment of 150 μm additivated LDPE films upon vapam-WOM exposure

| | Time of exposure (hours) | | | | |
|---|---|---|---|---|---|
| Film No. | 0 | 550 | 1770 | 2565 | 4484 |
| Film 1[a)] | 0.000 | 0.018 | 0.034 | 0.043 | 0.064 |
| Film 2[a)] | 0.000 | 0.011 | 0.023 | 0.028 | not measured |
| Film 5[b)] | 0.000 | 0.013 | 0.038 | 0.054 | 0.073 |
| Film 6[b)] | 0.000 | 0.021 | 0.045 | 0.063 | 0.131 |

Footnotes are listed at table 1.

TABLE 5

Tensile measurements of 150 μm additivated LDPE films upon vapam-WOM exposure

| Film No. | Time of exposure (hours) | | | | |
|---|---|---|---|---|---|
| | 0 | 620 | 1245 | 2275 | 4200 |
| Film 1[a] | 100 | 100 | 97 | 95 | 92 |
| Film 2[a] | 100 | 100 | not measured | 97 | 90 |
| Film 4[b] | 100 | 98 | not measured | 88 | 85 |
| Film 5[b] | 100 | 100 | 100 | 94 | 87 |
| Film 6[b] | 100 | 95 | 92 | 76 | 65 |

Footnotes are listed at table 1.

Example 11

Flame Retardancy of Polypropylene Films

PP Film Manufacture:

Unless stated otherwise, commercial polypropylene (Moplen HP 552 R, manufacturer: Basell) is processed on a co-rotating extruder type Berstorff 32D (lab size twin screw extruder, 25 mm screw diameter, 9 heating zones) at a maximum temperature Tmax of 230° C. with a throughput rate of about 12 kg/h for 120 rpm screw speed and the additives indicated in Table 6. After cooling in a water bath the polymer strand is granulated.

Test specimens are prepared by cast film extrusion (150 μm thickness) using a cast film equipment Tech-line CR 72T coupled with an extruder Tech-line E 20 T from Collin.

The calculated final concentrations in the PP films are indicated in Table 6.

TABLE 6

Concentration of added additive in the PP film

| Film No. | Additive |
|---|---|
| Film 7[b] | without addition |
| Film 8[a] | 0.5% compound P-201 |
| Film 9[a] | 1.0% compound P-201 |
| Film 10[a] | 0.5% compound P-204 |
| Film 11[a] | 1.0% compound P-204 |

Footnotes are listed at table 1.

Performances of Additives as Flame Retardants in PP Film:

DIN4102-B2: The test samples are investigated for flame retardancy in accordance to a modified DIN 4102-B2 (edge ignition) test, wherein the modification is the length of 160 mm instead of 190 mm for the text specimen, i.e. 160 mm height and 60 mm width as specimen dimensions. There are two basic results: not classified and B2.

UL94-VTM: The test samples are investigated for flame retardancy according to UL94-VTM. There are 4 basic results: not classified, VTM2, VTM1 and VTM0. VTM0 represents the best basic result.

TABLE 7

Flaming test on 150 μm PP cast films according to modified DIN 4102-B2 (edge ignition)

| Film No. | Burning time [sec] | Damaged length [mm] | Burning drips paper ignition[f] | DIN4102-B2 rating |
|---|---|---|---|---|
| Film 7[b] | 12 | 120 | yes | not classified |
| Film 8[a] | 4.0 | 73 | no | B2 |
| Film 9[a] | 3.6 | 72 | no | B2 |

TABLE 7-continued

Flaming test on 150 μm PP cast films according to modified DIN 4102-B2 (edge ignition)

| Film No. | Burning time [sec] | Damaged length [mm] | Burning drips paper ignition[f] | DIN4102-B2 rating |
|---|---|---|---|---|
| Film 10[a] | 2.4 | 69 | no | B2 |
| Film 11[a] | 4.0 | 60 | no | B2 |

Footnotes [a] and [b] are listed at table 1.

[f] Rated 'yes', if the burning drips dripping from the ignited test specimen ignite paper placed underneath the test specimen according to the DIN 4102-B2 test norm.

Low values for burning time and damaged length reflect increased flame retardancy.

TABLE 8

Flaming test on 150 μm PP cast films according to UL94-VTM

| Film No. | Total burning time [sec] | Burning drips cotton ignition[g] | UL94-VTM rating |
|---|---|---|---|
| Film 7[b] | 19 | 5 (5) | not classified |
| Film 8[a] | 9 | 3 (5) | VTM2 |
| Film 9[a] | 4 | 0 (5) | VTM0 |
| Film 10[a] | 6 | 4 (5) | VTM2 |
| Film 11[a] | 4 | 0 (5) | VTM0 |

Footnotes [a] and [b] are listed at table 1.

g): Number of tests (out of five tests) in which burning drips dripping from the ignited test specimen ignite cotton placed underneath the test specimen according to the UL94-VTM test norm.

Low values for total burning time and less burning drips igniting cotton reflect increased flame retardancy.

The invention claimed is:

1. A compound of formula I

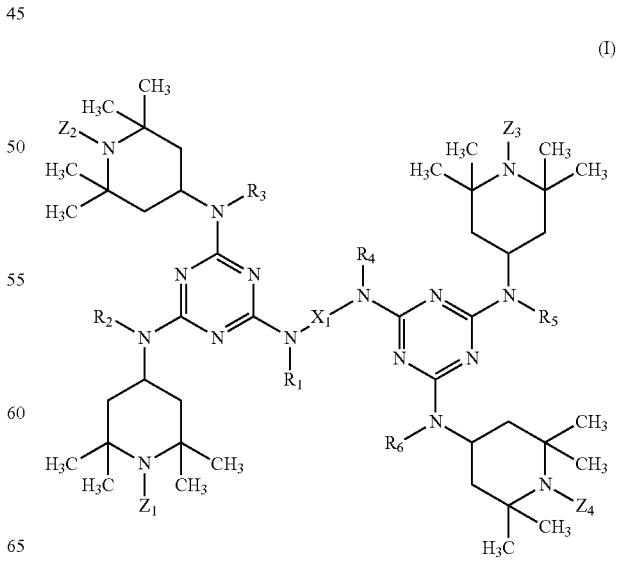

wherein
R₁ is a group of formula III

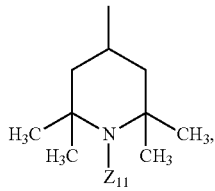
(III)

hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

R₄ is a group of formula IV

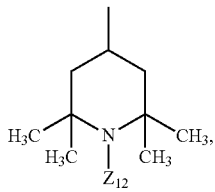
(IV)

hydrogen, $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

R₂, R₃, R₅ and R₆ are each independently from each other $C_1$-$C_{18}$ alkyl, $C_3$-$C_{18}$ alkenyl, $C_3$-$C_{12}$ cycloalkyl, $C_5$-$C_8$ cycloalkenyl, $C_6$-$C_{10}$ bicycloalkyl, $C_3$-$C_{18}$ alkynyl, $C_6$-$C_{10}$ aryl, $C_7$-$C_9$ aralkyl or $C_7$-$C_{20}$ aralkyl substituted by $C_1$-$C_4$ alkyl or $C_6$-$C_{10}$ aryl;

$Z_1$, $Z_2$, $Z_3$, $Z_4$, $Z_{11}$ and $Z_{12}$ are each independently from each other $C_1$-$C_{18}$ alkyloxy, $C_3$-$C_{18}$ alkenyloxy, $C_3$-$C_{18}$ alkynyloxy, $C_6$-$C_{10}$ aryloxy, $C_7$-$C_9$ aralkyloxy or $C_7$-$C_{20}$ aralkyloxy substituted by $C_1$-$C_4$ alkyl or $C_6$-$C_{10}$ aryl; and $X_1$ is $C_5$-$C_{12}$ alkylene or $C_3$-$C_{12}$ alkylene substituted by hydroxyl.

2. The compound according to claim 1, wherein
R₁ is a group of formula III, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;
R₄ is a group of formula IV, hydrogen, $C_1$-$C_{12}$ alkyl, $C_3$-$C_{12}$ alkenyl, $C_5$-$C_8$ cycloalkyl, $C_5$-$C_7$ cycloalkenyl or benzyl;
R₂, R₃, R₅ and R₆ are each independently from each other $C_1$-$C_{12}$ alkyl, $C_3$-$C_{12}$ alkenyl, $C_5$-$C_8$ cycloalkyl, $C_5$-$C_7$ cycloalkenyl or benzyl;
$Z_1$, $Z_2$, $Z_3$, $Z_4$, $Z_{11}$ and $Z_{12}$ are each independently from each other $C_1$-$C_{12}$ alkyloxy, $C_3$-$C_{12}$ alkenyloxy or benzyloxy; and
$X_1$ is $C_5$-$C_8$ alkylene.

3. A compound according to claim 1, wherein
R₂, R₃, R₅ and R₆ are each independently from each other $C_1$-$C_{12}$ alkyl.

4. A compound according to claim 1, wherein
R₁ is a group of formula III, R₄ is a group of formula IV.

5. A compound according to claim 1, wherein
$Z_1$, $Z_2$, $Z_3$, $Z_4$, $Z_{11}$ and $Z_{12}$ are each independently from each other methyloxy, ethyloxy, propyloxy, octyloxy, undecyloxy or prop-2-enyloxy.

6. A compound according to claim 1, wherein
R₁ and R₄ are each independently from each other hydrogen, $C_1$-$C_{12}$ alkyl or $C_5$-$C_8$ cycloalkyl.

7. The compound according to claim 1, wherein
R₁ is a group of formula III or hydrogen;
R₄ is a group of formula IV or hydrogen;
R₂, R₃, R₅ and R₆ are each independently from each other $C_1$-$C_{12}$ alkyl;
$Z_1$, $Z_2$, $Z_3$, $Z_4$, $Z_{11}$ and $Z_{12}$ are each independently from each other $C_1$-$C_{12}$ alkyloxy, wherein in the case of $C_3$-$C_{12}$ alkyloxy, both carbon atoms in α- and β-position next to the oxygen are not branched; and
$X_1$ is $C_5$-$C_8$ alkylene.

8. A compound according to claim 1, wherein
$X_1$ is hexamethylene.

9. A compound of formula P-201 or P-204

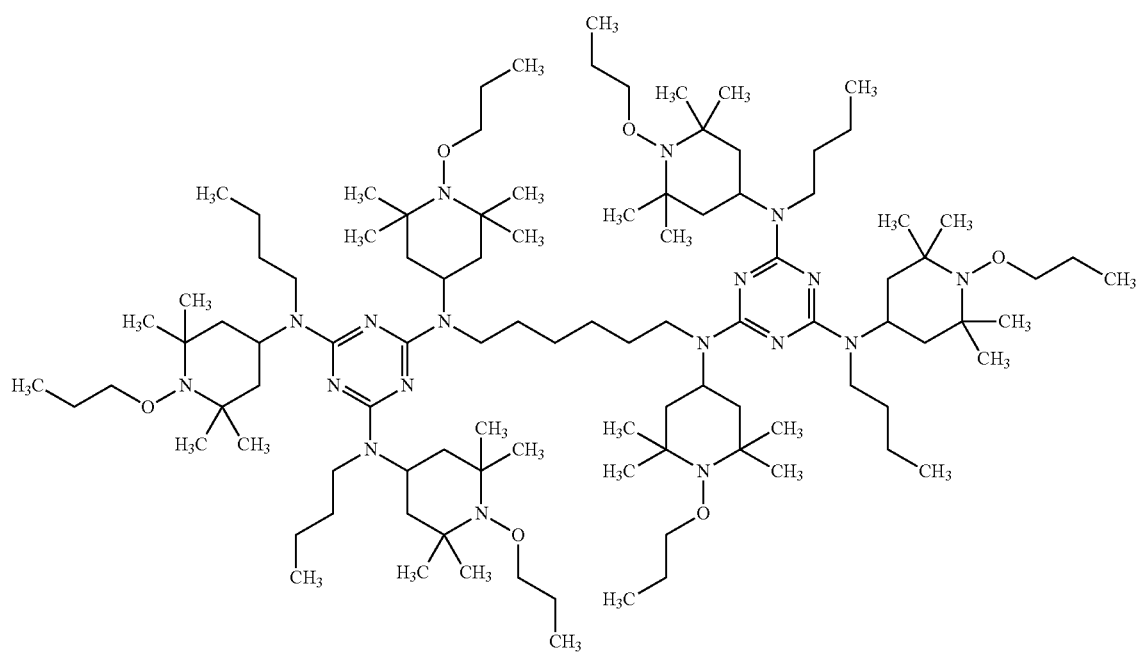
(P-201)

-continued

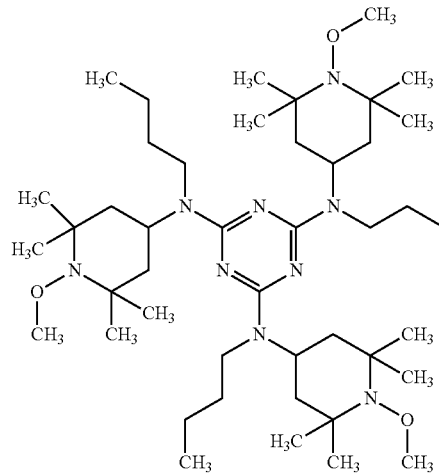
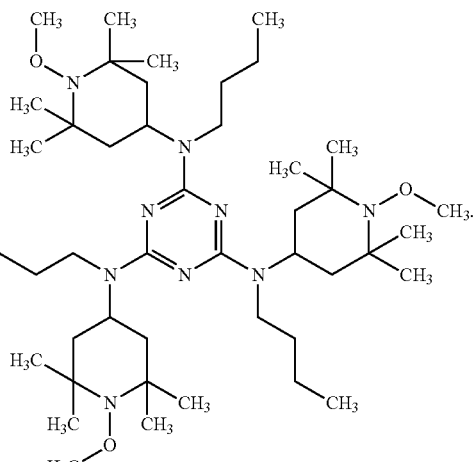

(P-204)

10. A composition comprising
a) an organic material which is susceptible to oxidative, thermal or light-induced degradation; and
b) at least one compound of the formula I according to claim 1.

11. A composition according to claim 10, wherein component b) is present in an amount of from 0.001 to 10% based on the weight of component a).

12. A composition according to claim 10, which contains further additives.

13. A composition according to claim 12, which contains a further additive selected from the group consisting of antioxidants, UV absorbers, hindered amine light stabilizers, nickel compounds, metal deactivators, phosphites or phosphonites, hydroxylamines, thiosynergists, nucleating agents, peroxide scavengers, fillers, reinforcing agents and terpene derivatives.

14. A method for stabilization of an organic material susceptible to oxidative, thermal or light-induced degradation, which comprises the incorporation therein or applying thereto a compound of formula I according to claim 1.

15. A method for improving flame retardancy of an organic material, which comprises the incorporation therein or applying thereto a compound of formula I according to claim 1.

* * * * *